United States Patent [19]
Branca et al.

[11] Patent Number: 5,278,161
[45] Date of Patent: Jan. 11, 1994

[54] AMINO ACID DERIVATIVES USEFUL AS RENIN INHIBITORS

[75] Inventors: Quirico Branca, Basle, Switzerland; Marie-Paule Heitz, St. Louis, France; Marcel Müller, Frenkendorf, Switzerland; Werner Neidhart, Freiburg im Breisgau, Fed. Rep. of Germany; Stadler Heinz, Rheinfelden, Switzerland; Eric Vieira, Basle, Switzerland; Wolfgang Wostl, Grenzach-Wyhlen, Fed. Rep. of Germany

[73] Assignee: Hoffmann-La Roche Inc., Nutley, N.J.

[21] Appl. No.: 971,787

[22] Filed: Nov. 5, 1992

Related U.S. Application Data

[63] Continuation of Ser. No. 718,071, Jun. 20, 1991, abandoned.

[30] Foreign Application Priority Data

Jun. 28, 1990 [CH] Switzerland ............... 2159/90

[51] Int. Cl.$^5$ ............... C07D 487/04; C07D 471/04; C07D 263/06; A61K 31/495
[52] U.S. Cl. ............... 514/249; 514/248; 514/300; 514/303; 544/236; 544/350; 544/405; 546/119; 546/121; 546/336; 548/215; 564/374; 564/453
[58] Field of Search ............ 544/350; 514/249

[56] References Cited

U.S. PATENT DOCUMENTS 4,921,855  5/1990  Hemmi et al. ............... 514/235.8
5,134,123  7/1992  Branca et al. ............... 514/18

FOREIGN PATENT DOCUMENTS 9061360  9/1989  Australia .
0266950  5/1988  European Pat. Off. .
0300189  1/1989  European Pat. Off. .
0332008  9/1989  European Pat. Off. .
 369743  5/1990  European Pat. Off. .
 416373  3/1991  European Pat. Off. .

OTHER PUBLICATIONS

Bradbury et al, *Chemical Abstracts*, vol. 114, No. 81884 (1991).
Bradbury et al, *Chemical Abstracts*, vol. 115, No. 49624 (1991).
Roberts et al., *J. Med. Chem.* 33, p. 2326 (Sep. 1990).
*Advanced Organic Chemistry* by Jerry March (2nd Ed.) pp. 382–387 (1977).
Kubo et al. Chem. Pharm. Bull. 36, p. 4355 (1988).
Ochiai et al. Chem. Abstr. vol. 50, 7810d (1956).
Wermuth et al Chim. Ther. 6, 109 (1971).
Nohara et al. Tetrahedron Letters 1974, 1183.
Org. Synthesis (Andrew S. Kende, Editor-in-Chief) 64, 19 (1986), (John Wiley & Sons Publ.).
Plattner et al. J. Med. Chem. 31 (12), 2277, 1988.
Braude et al J. C. S. 1950 (2014).
Gomez-Parra et al Arch. Pharm. 317, 183 (1984).
Hui et al J. Med. Chem. 1987, 30, 1287–1295.

*Primary Examiner*—Mukund J. Shah
*Assistant Examiner*—E. Bernhardt
*Attorney, Agent, or Firm*—George M. Gould; George W. Johnston; Ellen Ciambrone Coletti

[57] ABSTRACT

Compounds of the formula

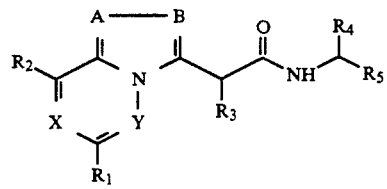

wherein A, B, X, Y, $R^1$, $R^2$, $R^3$, $R^4$ and $R^5$ are as set forth in the specification, in the form of optically pure diastereomers, mixtures of diastereomers, diastereomeric racemates or mixtures of diastereomeric racemates as well as pharmaceutically acceptable salts thereof which inhibit the activity of the natural enzyme renin and are useful in the control or prevention of high blood pressure and cardiac insufficiency are described.

55 Claims, No Drawings

AMINO ACID DERIVATIVES USEFUL AS RENIN INHIBITORS

This is a continuation of application Ser. No. 07/718,071 filed Jun. 20, 1991 now abandoned.

BRIEF SUMMARY OF THE INVENTION

The present invention relates to amino acid derivatives of the formula

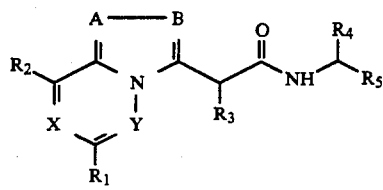

I wherein
one of A and B is nitrogen and the other is —CH— or both A and B are nitrogen,
one of X and Y is nitrogen and the other is —CH— or both X and Y are —CH—,
$R^1$ is phenyl, pyridyl or thienyl,
$R^2$ is alkyl or arylalkyl,
$R^3$ is hydrogen, alkyl, imidazol-2-ylmethyl, imidazol-4-ylmethyl, pyridylmethyl, pyrazol-3-ylmethyl, thien-2-ylmethyl, thiazol-4-ylmethyl, alkylthiomethyl, carbamoylmethyl, carbamoylethyl or benzyl,
$R^4$ is cyclohexylmethyl, benzyl or isobutyl and
$R^5$ is selected from the group consisting of

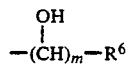 (a)

and

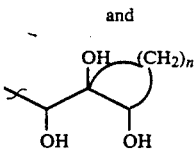 (b)

in which $R^6$ is cycloalkyl, alkyl, alkenyl or arylalkyl, m is the number 2 or 3 and n is the number 3 or 4, in the form of optically pure diastereomers, mixtures of diastereomers, diastereomeric racemates or mixtures of diastereomeric racemates as well as pharmaceutically acceptable salts of these compounds.

DETAILED DESCRIPTION OF THE INVENTION

The present invention relates to amino acid derivatives of the formula

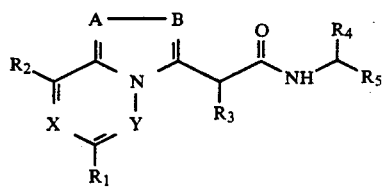

I wherein
one of A and B is nitrogen and the other is —CH— or both A and B are nitrogen,
one of X and Y is nitrogen and the other is —CH— or both X and Y are —CH—,
$R^1$ is phenyl, pyridyl or thienyl,
$R^2$ is alkyl or arylalkyl,
$R^3$ is hydrogen, alkyl, imidazol-2-ylmethyl, imidazol-4-ylmethyl, pyridylmethyl, pyrazol-3-ylmethyl, thien-2-ylmethyl, thiazol-4-ylmethyl, alkylthiomethyl, carbamoylmethyl, carbamoylethyl or benzyl,
$R^4$ is cyclohexylmethyl, benzyl or isobutyl and
$R^5$ is selected from the group consisting of

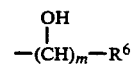 (a)

and

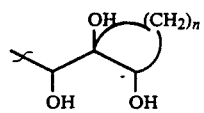 (b)

in which $R^6$ is cycloalkyl, alkyl, alkenyl or arylalkyl, m is the number 2 or 3 and n is the number 3 or 4, in the form of optically pure diastereomers, mixtures of diastereomers, diastereomeric racemates or mixtures of diastereomeric racemates as well as pharmaceutically acceptable salts of these compounds.

Objects of the present invention are the compounds of formula I and their pharmaceutically acceptable salts, the process for making these compounds, medicaments containing the compounds of formula I and the process of making such medicaments, as well as the use of compounds of formula I and their pharmaceutically acceptable salts in the control or prevention of illnesses or in the improvement of health, especially in the control or prevention of high blood pressure and cardiac insufficiency.

The term "alkyl" used in the present description, alone or in combination, denotes straight-chain and branched hydrocarbon residues with 1-8, preferably 1-4, carbon atoms, such as, for example, methyl, ethyl, n-propyl, isopropyl, n-butyl, isobutyl, sec.-butyl, t-butyl, pentyl, hexyl and the like. The term "alkoxy" denotes alkyl ether groups in which the term "alkyl" has the above significance, such as, for example, methoxy, ethoxy, propoxy, isopropoxy, butoxy, isobutoxy, sec.-butoxy, t-butoxy and the like. The term "cycloalkyl" denotes saturated, cyclic hydrocarbon residues with 3-8, preferably 3-6, carbon atoms, such as, for example, cyclopropyl, cyclobutyl, cyclopentyl, cyclohexyl and the like. The term "alkenyl" denotes straight-chain and branched, unsaturated hydrocarbon residues with 2-8, preferably 2-4, carbon atoms, such as, for example, vinyl, allyl, 2-butenyl, 3-butenyl and the like. The term "alkanoyloxy" denotes the acid residue of a straight-chain or branched alkanoic acid with 1-8, preferably 1-4, carbon atoms attached via an oxygen atom, such as, for example, formyloxy, acetyloxy, propionyloxy, butyryloxy, valeryloxy, isovaleryloxy and the like. The term "arylalkyl" denotes straight-chain or branched alkyl groups in which one or more hydrogen atoms have been replaced by aryl groups. The term "aryl" denotes a mono- or bicyclic aromatic hydrocarbon residue with 6-14 carbon atoms which is unsubstituted or mono- or multiply-substituted by alkyl, alkoxy, alkanoyloxy, amino, alkylamino, dialkylamino, alkylcarbonylamino, hydroxy, halogen, trifluoromethyl or nitro, such as, for example, phenyl, α- or β-naphthyl, idenyl, anthryl or phenanthryl and the like. Examples of arylalkyl groups are benzyl, diphenylmethyl, trityl, α- or β-naphthylmethyl, 2-phenylethyl, 3-phenyl-2-propyl, 4-phenyl-3-butyl, 2-(α- or β-naphthyl)ethyl, 3-α-naphthyl-2-propyl, 4-α-naphthyl-3-butyl and the like, whereby the aromatic residue can in each case be mono- or multiply- substituted as indicated above.

The term "pharmaceutically acceptable salts" includes salts with inorganic or organic acids such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like. Such salts can be prepared readily by any person skilled in the art.

The compounds of formula I contain at least three asymmetric carbon atoms and are therefore present in the form of optically pure diastereomers, mixtures of diastereomers, diastereomeric racemates or mixtures of diastereomeric racemates. The present invention embraces all forms. Mixtures of diastereomers, diastereomeric racemates or mixtures of diastereomeric racemates can be separated according to known methods, for example, by column chromatography, thin-layer chromatography, high performance liquid chromatography (HPLC) and the like.

Those compounds of formula I in which A and B each are nitrogen are preferred. X preferably is nitrogen and Y preferably is —CH—. Compounds of formula I in which $R^1$ is pyridyl, especially 3-pyridyl, are also preferred. $R^2$ preferably is alkyl or phenylalkyl, especially propyl, isopropyl, isobutyl, 1-methylpropyl or benzyl. $R^3$ preferably is hydrogen, imidazol-2-yl-methyl, imidazol-4-ylmethyl or pyridylmethyl, especially imidazol-4-ylmethyl or pyridyl-3-methyl. Cyclohexymethyl is the preferred meaning for $R^4$. $R^5$ preferably signifies group (a). The preferred meaning for m is the number 2 and the preferred meaning for $R^6$ is cycloalkyl.

From the above it follows that there are particularly preferred those compounds of formula I in which A, B and X each are nitrogen, Y is —CH—, $R^1$ is 3-pyridyl, $R^2$ is propyl, isopropyl, isobutyl, 1-methylpropyl or benzyl, $R^3$ is imidazol-4-ylmethyl or pyridyl-3-methyl, $R^4$ is cyclohexyl-methyl and $R^5$ is group (a) in which m is the number 2 and $R^6$ is cycloalkyl.

Especially preferred compounds of formula I are:
(R or S)-N-[(1S,2R,3S)-1-(Cyclohexylmethyl)-3-cyclopropyl-2,3-dihydroxypropyl]-8-propyl-α,6-bis(3-pyridyl)-s-triazolo[4,3-a]pyrazine-3-acetamide,
(R or S)-N-[(1S,2R,3S)-1-(cyclohexylmethyl)-3-cyclopropyl-2,3-dihydroxypropyl]-8-isopropyl-α-(imidazol-4-ylmethyl)-6-(3-pyridyl)-s-triazolo[4,3-a]pyrazine-3-acetamide,
(R or S)-N-[(1S,2R,3S)-1-(cyclohexylmethyl)-3-cyclohexyl-2,3-dihydroxypropyl]-α-(imidazol-4-ylmethyl)-8-isobutyl-6-(3-pyridyl)-s-triazolo[4,3-a]pyrazine-3-acetate,
(R or S)-N-[(1S,2R,3S)-1-(cyclohexylmethyl)-2,3-dihydroxy-5-methylhexyl]-8-propyl-6-(3-pyridyl)-α-(3-pyridylmethyl)-s-triazolo[4,3-a]pyrazine-3-acetamide,
(S or R)-N-[(1S,2R,3S)-1-(cyclohexylmethyl)-3-cyclopropyl-2,3-dihydroxypropyl]-8-[(RS)-1-methylpropyl]-α-(3-pyridylmethyl)-6-(3-pyridyl)-s-triazolo[4,3-a]pyrazine-3-acetamide and
N-[(1S,2R,3S)-1-(cyclohexylmethyl)-3-cyclopropyl-2,3-dihydroxypropyl]-8-[(RS)-1-methylpropyl]-6-(3-pyridyl)-s-triazolo[4,3-a]pyrazine-3-carboxamide.

The compounds of formula I in the form of optically pure diastereomers, mixtures of diastereomers, diastereomeric racemates or mixtures of diastereomeric racemates as well as pharmaceutically acceptable salts thereof can be prepared by
a) reacting a compound of the general formula

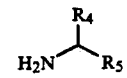

wherein $R^4$ and $R^5$ have the significance given above, with a compound of the general formula

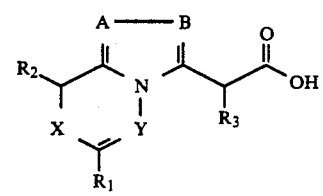

wherein A, B, X, Y, $R^1$, $R^2$ and $R^3$ have the significance given above,
or an activated derivative thereof, and b) if desired, separating a mixture of diastereomeric racemates into the diastereomeric racemates or optically pure diastereomers, and/or c) if desired, separating a mixture of diastereomers into the optically pure diastereomers, and/or d) if desired, converting a compound obtained into a pharmaceutically acceptable salt.

The acylation of a compound of formula II is effected according to known methods. Especially suitable acylating agents are activated acid derivatives, such as, for example, esters, mixed esters, acid halides and acid anhydrides or mixed anhydrides. The reaction is carried out in an organic solvent or solvent mixture which is inert under the reaction conditions at a temperature between about 0° C. and room temperature. As solvents there come into consideration especially aromatic hydrocarbons such as benzene, toluene or xylene, chlorinated hydrocarbons such as methylene chloride or chloroform, ethers such as diethyl ether, tetrahydrofuran or dioxan, and the like. The reaction is effected under reaction conditions which are usual in peptide chemistry, for example, preferably in the presence of a condensation agent, such as, for example, HBTU (O-benzotriazolyl-N,N,N',N'-tetramethyluronium hexafluorophosphate), BOP (benzotriazol-1-yloxy-tris(dimethylamino)phosphonium hexafluorophosphate), BOPC (bis(2-oxo-2-oxozolidinyl)phosphine chloride), HOBT (N-hydroxybenzotriazole), DBU (1,8-diazabicyclo[5.4.0]-undec-7-ene), DCC (dicyclohexylcarbodiimide), EDC (N-ethyl-N'(3-dimethylaminopropyl)carbodiimide hydrochloride), Hünig base (ethyldiisopropylamine), and the like. The reaction is conveniently carried out in an organic solvent or solvent mixture which is inert under the reaction conditions at a temperature between about 0° C. and 50° C., preferably at about room temperature. As solvents there come into consideration especially dimethylformamide, methylene chloride, aceto-nitrile, tetrahydrofuran, and the like.

The starting materials of formula II in which $R^5$ is group (a) and wherein m is the number 3, or $R^5$ is group (b), are novel and are also an object of the present invention. They can be prepared, for example, by simultaneously cleaving off the amino protecting group and the O-protecting group in a compound of the general formulas

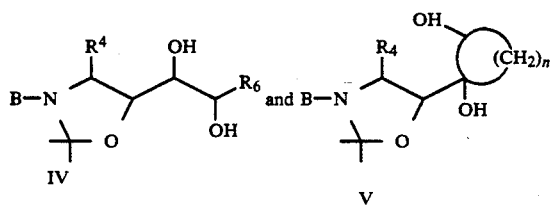

wherein B is an amino protecting group, preferably t-butoxycarbonyl or benzyloxycarbonyl, and $R^4$, $R^6$ and n have the significance given above.

The cleavage of the N-protecting group and O-protecting group is also effected according to known methods, for example, in an organic solvent or solvent mixture which is inert under the reaction conditions at a temperature between about 0° C. and room temperature using an acid such as hydrochloric acid, trifluoroacetic acid, and the like. Suitable solvents are ethers such as tetrahydrofuran or dioxan, alcohols such as methanol or chlorinated hydrocarbons such as methylene chloride, and the like. Under these reaction conditions the oxazolidine ring is, as already mentioned, simultaneously cleaved.

The starting materials of formula II in which $R^5$ is (a), and wherein m is the number 2, are known or can be obtained in a manner analogous to the preparation of the known compounds.

The compounds of formulas IV and V are also novel and are objects of the present invention. They can be prepared according to different known methods starting from compounds of formula VI. These preparative procedures are compiled in Scheme I hereinafter. In this Scheme Met is a metal such as lithium or magnesium and B, $R^4$, $R^6$ and n have the significance as given above. With respect to the precise reaction conditions reference is made to the experimental section.

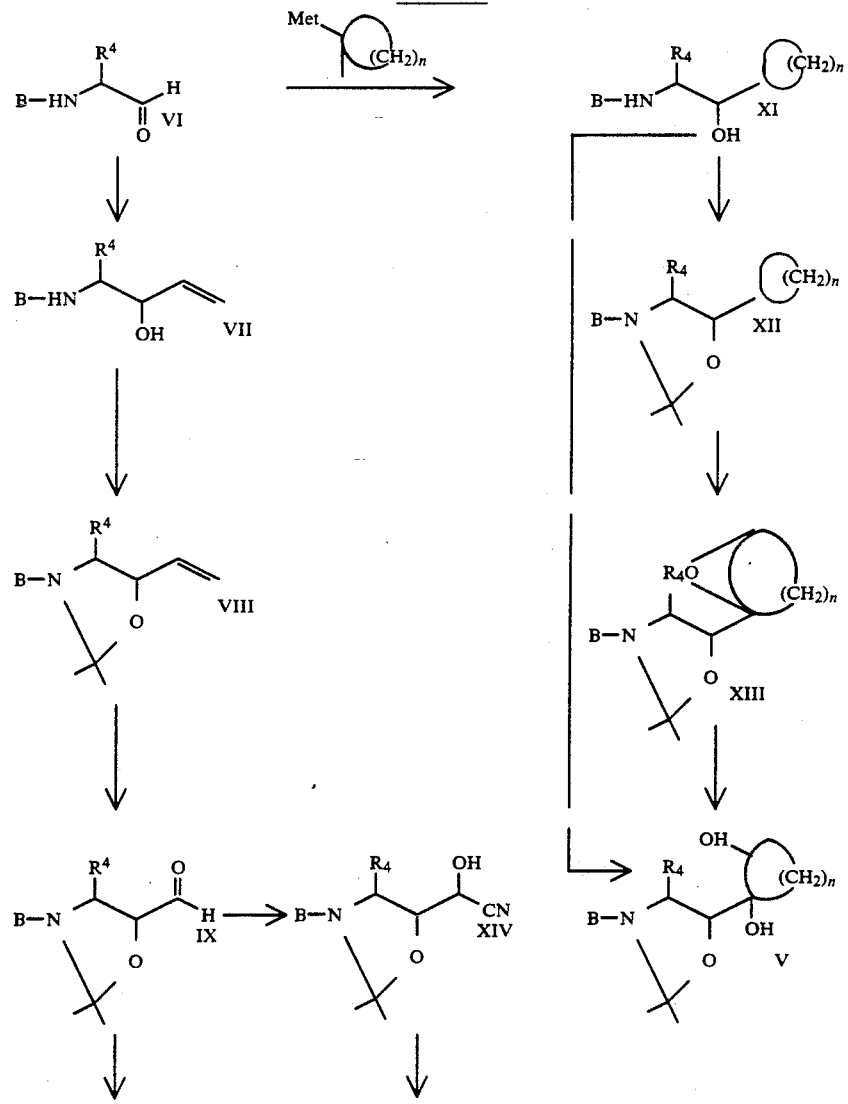

Scheme I

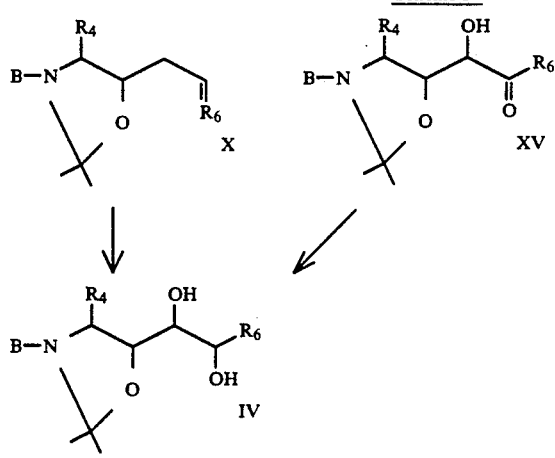

The starting materials of formula III in which A, B and X each are nitrogen and Y is —CH— are described in EP-A 0.369.743 or can be obtained in a manner analogous to the preparation of the known compounds.

The remaining compounds of formula III are also novel and are an object of the present invention. They can be prepared starting from corresponding pyrazinones, pyridazinones and pyridinones according to various known methods and which are in part analogous to the process described in EP-A 0.369.743. These preparative procedures as well as the process according to EP-A 0.369.743 are compiled in Schemes II–IV hereinafter. In these Schemes R is alkyl and A, B, $R^1$, $R^2$ and $R^3$ have the significance given above. The pyrazinones of formula XVI in Scheme II and the pyridazinones of formula XXIV in Scheme III as well as their preparation are described in part in EPA 0.369.743 or Chim. Ther., 6, 109 (1971) or can be obtained in a manner analogous to the preparation of the known compounds. The pyridinones of formula XXXII in Scheme IV are novel, but belong to a known class of substance. They can be prepared in a manner analogous to the preparation of the compounds described in Tetrahedron Letters 1974, 1183 and Arch. Pharm., 317, 183 (1984).

Scheme II

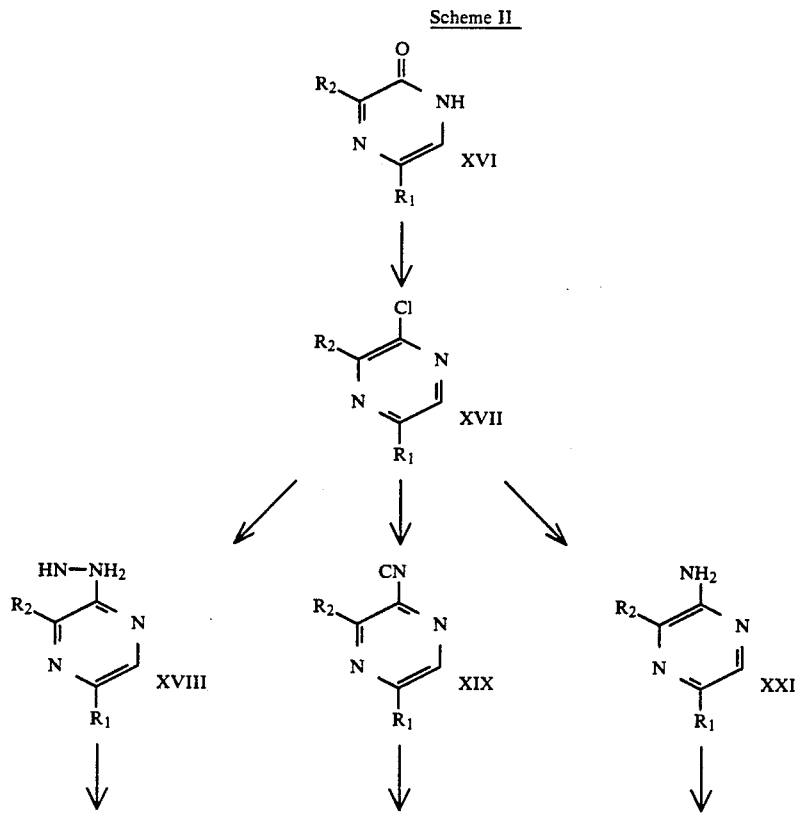

Scheme II
cf. EPA 0.369.743
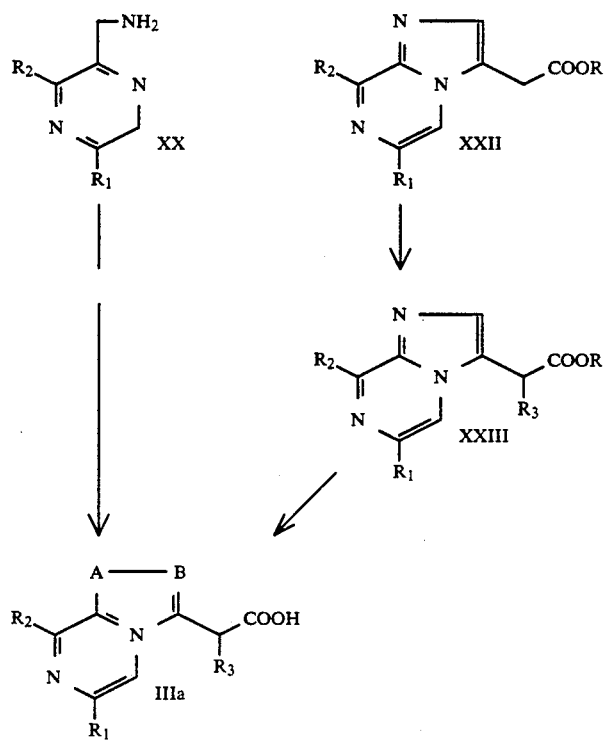
Scheme III
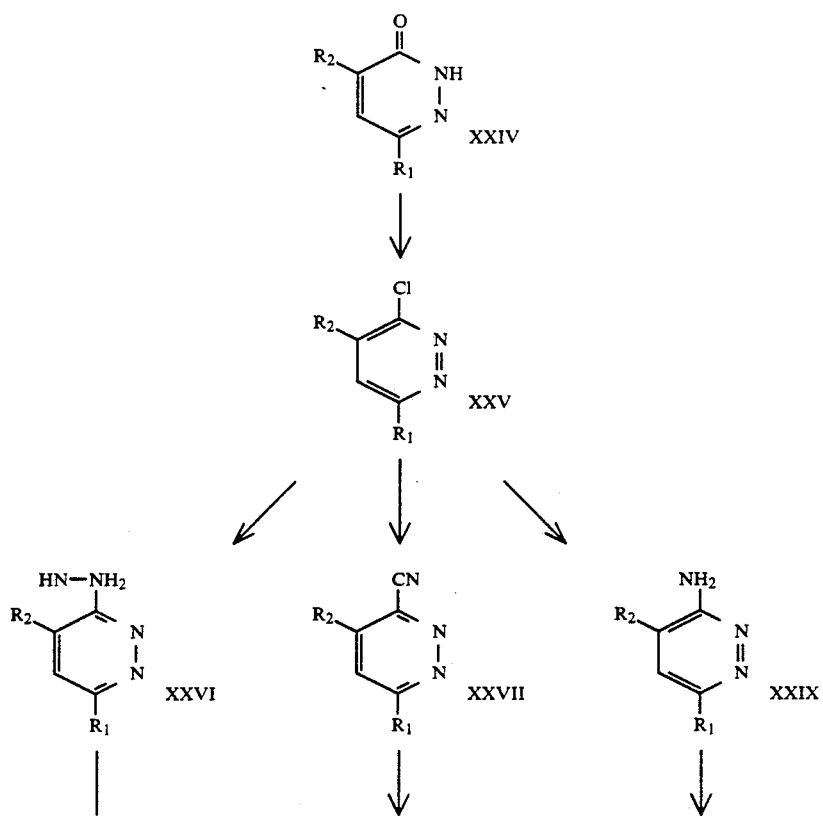

Scheme III
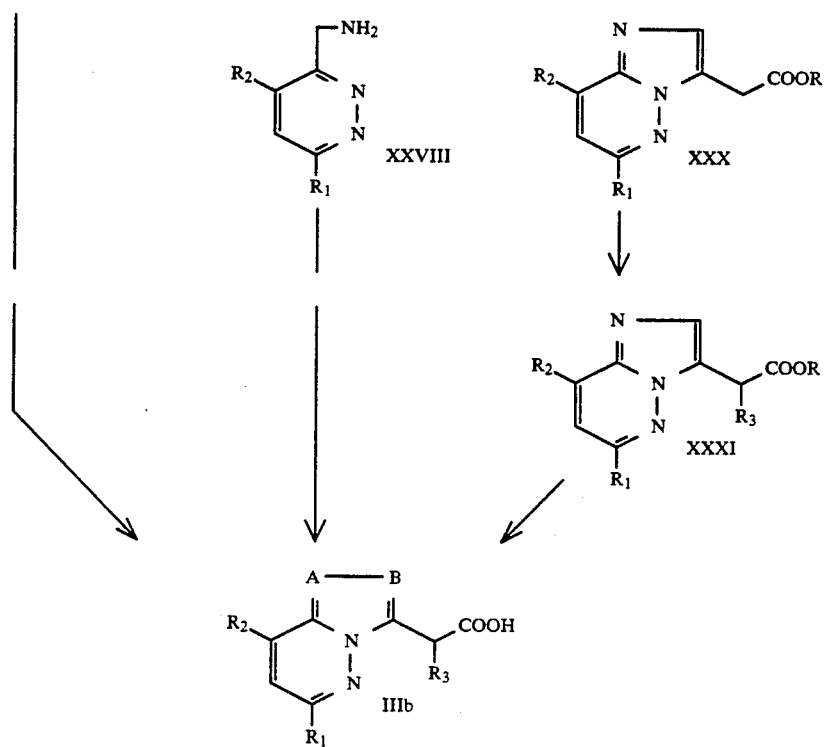
Scheme IV
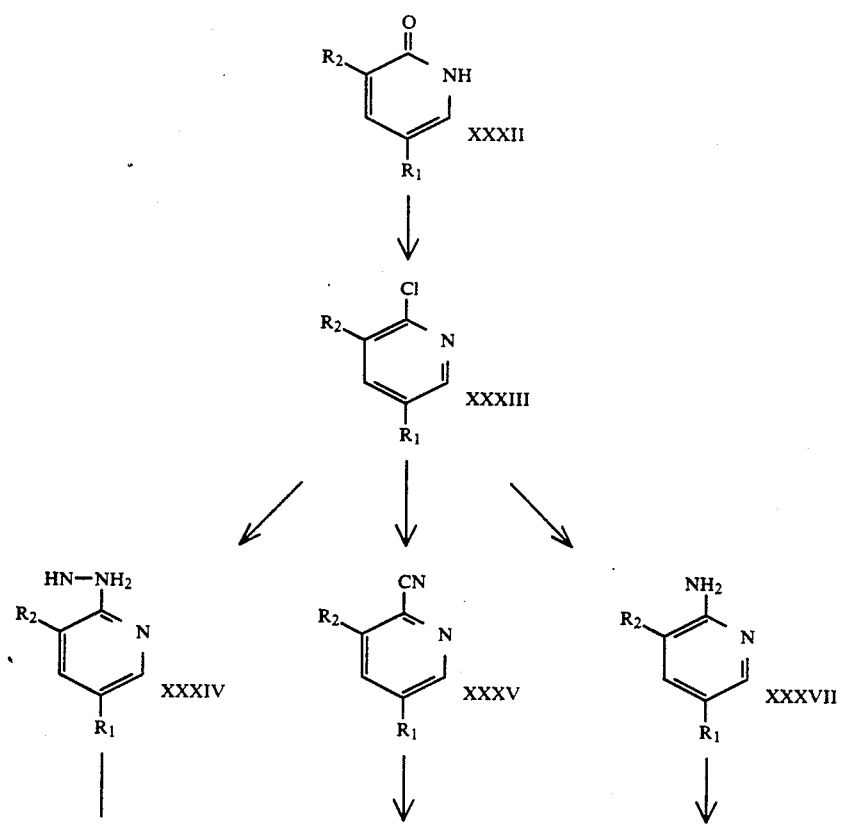

-continued

Scheme IV

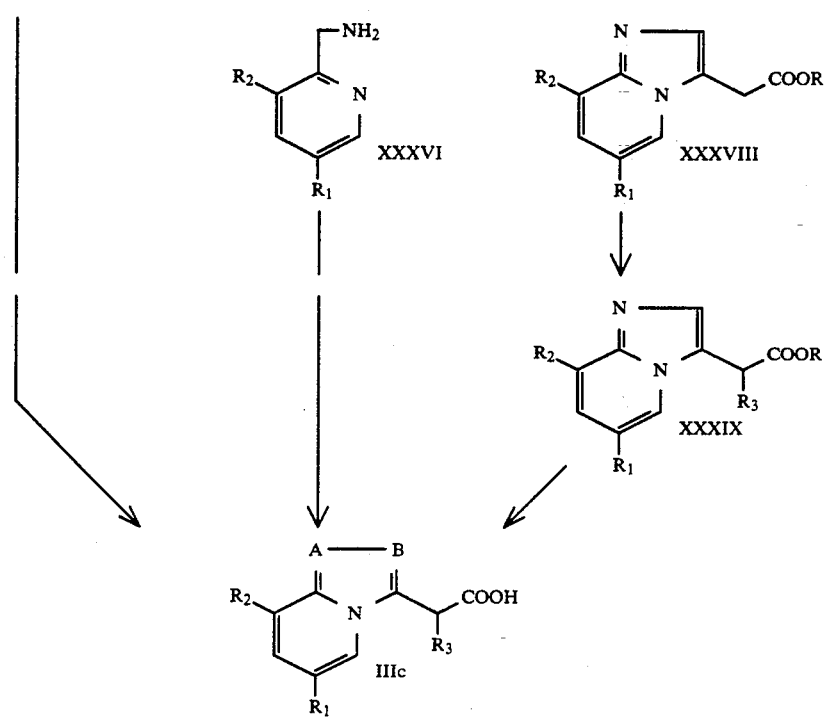

The compounds of formula I and their pharmaceutically acceptable salts have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angiotensin II increases the blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II itself or to the heptapeptide angiotensin III which is formed therefrom as a cleavage product. Inhibition of the enzymatic activity of renin brings about a decrease in the formation of angiotensin I and as a consequence thereof the formation of a smaller amount of angiotensin II. The reduced concentration of this active peptide hormone is the actual reason for the blood pressure-lowering activity of renin inhibitors.

The activity of renin inhibitors can be demonstrated experimentally by means of the in vitro test described hereinafter:

IN VITRO TEST WITH PURE HUMAN RENIN

The test is carried out in Eppendorf test tubes. The incubation mixture consists of (1) 100 µl of human renin in buffer A (0.1M sodium phosphate solution, pH 7.4, containing 0.1% bovine serum albumin, 0.1% sodium azide and 1 mM ethylenediaminetetraacetic acid), sufficient for a renin activity of 2-3 ng of angiotensin I/ml/hr.; (2) 145 µl of buffer A; (3) 30 µl of 10 µM human tetradecapeptide renin substrate (hTD) in 10 mM hydrochloric acid; (4) 15 µl of dimethyl sulphoxide with or without inhibitor and (5) 10 µl of a 0.03 molar solution of hydroxyquinoline sulphate in water.

The samples are incubated for three hours at 37° C. or 4° C. in triplicate. 2×100 µl samples per experimental test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I is determined by the difference between the experiment at 37° C. and that at 4° C.

The following controls are carried out:
(a) Incubation of hTD samples without renin and without inhibitor at 37° C. and 4° C. The difference between these two values gives the base value of the angiotensin I production.
(b) Incubation of hTD samples with renin, but without inhibitor at 37° C. and 4° C. The difference between these values gives the maximal value of angiotensin I production.

In each sample the base value of the angiotensin I production is subtracted from the angiotensin I production which is determined. The difference between the maximal value and the base value gives the value of the maximal substrate hydrolysis (=100%) by renin.

The results are given as $IC_{50}$ values which denote that concentration of the inhibitor at which the enzymatic activity is inhibited by 50%. The $IC_{50}$ values are determined from a linear regression curve from a logit-log plot.

The results obtained in this test are compiled in the following Table:

TABLE

| Compound | $IC_{50}$ value in nmol/lt |
|---|---|
| A | 61 |
| B | 43 |
| C | 42 |
| D | 57 |

TABLE -continued

| Compound | IC$_{50}$ value in nmol/lt |
|---|---|
| E | 48 |
| F | 11 |

A = (R or S)-N-[(1S,2R,3S)-1-(Cyclohexylmethyl)-3-cyclopropyl-2,3-dihydroxypropyl]-8-propyl-α,6-bis(3-pyridyl)-s-trizolo[4,3-a]pyrazine-3-acetamide.
B = (R or S)-N-[(1S,2R,3S)-1-(Cyclohexylmethyl)-3-cyclopropyl-2,3-dihydroxypropyl]-8-isopropyl-α-(imidazol-4-ylmethyl)-6-(3-pyridyl)-s-trazolo[4,3-a]pyrazine-3-acetamide.
C = (R or S)-N-[(1S,2R,3S)-1-(Cyclohexylmethyl)-3-cyclohexyl-2,3-dihydroxypropyl]-a-(imidazol-4-ylmethyl)-8-isobutyl-6-(3-pyridyl)-s-trizolo[4,3-a]pyrazine-3-acetate.
D = (R or S)-N-[(1S,2R,3S)-1-(Cyclohexylmethyl)-2,3-dihydroxy-5-methylhexyl]-8-propyl-6-(3-pyridyl)-α-(3-pyridylmethyl)-s-trizolo[4,3-a]pyrazine-3-acetamide.
E = (S or R)-N-[(1S,2R,3S)-1-(Cyclohexylmethyl)-3-cyclopropyl-2,3-dihydroxypropyl]-8[(RS)-1-methylpropyl]-α-(3-pyridylmethyl)-6-(3-pyridyl)-s-trizolo[4,3-a]pyrazine-3-acetamide.
F = N-[(1S,2R,3S)-1-(Cyclohexylmethyl)-3-cycloproply-2,3-dihydroxypropyl]-8-[(RS)-1-methylpropyl]-6-(3-pyridyl)-s-triazolo[4,3-a]pyrazine-3-carboxamide.

The compounds of formula I as well as their pharmaceutically acceptable salts can be used as medicaments, for example, in the form of pharmaceutical preparations. The pharmaceutical preparations can be administered enterally such as orally, for example, in the form of tablets, coated tablets, dragees, hard and soft gelatin capsules, solutions, emulsions or suspensions, nasally, for example, in the form of nasal sprays, or rectally, for example, in the form of suppositories. However, the administration can also be effected parenterally such as intramuscularly or intravenously, for example, in the form of injectable solutions.

For the manufacture of tablets, coated tablets, dragees and hard gelatine capsules the compounds of formula I as well as their pharmaceutically acceptable salts can be processed with pharmaceutically inert, inorganic or organic excipients. Lactose, maize starch or derivatives thereof, talc, stearic acid or its salts and the like can be used as excipients for tablets, dragees and hard gelatin capsules.

Suitable excipients for soft gelatin capsules are, for example, vegetable oils, waxes, fats, semi-solid and liquid polyols and the like.

Suitable excipients for the manufacture of solutions and syrups are, for example, water, polyols, saccharose, invert sugar, glucose and the like.

Suitable excipients for injection solutions are, for example, water, alcohols, polyols, glycerol, vegetable oils and the like.

Suitable excipients for suppositories are, for example, natural or hardened oils, waxes, fats, semi-liquid or liquid polyols and the like.

Moreover, the pharmaceutical preparations can contain preserving agents, solubilizers, viscosity-increasing substances, stabilizing agents, wetting agents, emulsifying agents, sweetening agents, coloring agents, flavouring agents, salts for varying the osmotic pressure, buffers, coating agents or antioxidants. They can also contain other therapeutically valuable substances.

In accordance with the invention the compounds of general formula I as well as their pharmaceutically acceptable salts can be used in the control or prevention of high blood pressure and cardiac insufficiency. The dosage can vary within wide limits and will, of course, be fitted to the individual requirements in each particular case. In general, in the case of oral administration a daily dosage of about 3 mg to about 3 g, preferably about 10 mg to about 1 g, should be appropriate, for example, approximately 300 mg per person, divided in preferably 1-3 unit doses, containing preferably the same dose can be administered, however, the upper limit just given can also be exceeded when this is found to be indicated. Usually, children receive half of the adult dosage.

The following Examples are intended to illustrate the present invention, but are not intended to be limiting in any manner. All temperatures are given in degrees Celsius.

EXAMPLE 1

218 mg (0.56 mmol) of rac-8-propyl-6-(3-pyridyl)-α-(3-pyridylmethyl)-s-triazolo[4,3-a]pyrazine-3-acetic acid, 127 mg (0.56 mmol) of (1S,2R,3S)-3-amino-4-cyclohexyl-1-cyclopropyl-1,2-butanediol (EP-A 0.332.008) and 248 mg of (0.56 mmol) of benzotriazol-1-yloxy-tris-(dimethylamino)phosphonium hexafluorophosphate (BOP) are dissolved in 20 ml of methylene chloride (CH$_2$Cl$_2$), 0.192 ml (1.12 mmol) of Hünig base is added thereto and the solution is stirred at room temperature for 12 hours. Subsequently, it is partitioned between CH$_2$Cl$_2$ and saturated ammonium chloride solution, the organic phase is dried over sodium sulphate and finally the solvent is removed under reduced pressure.

The crude product (600 mg of yellow oil), which contains the desired product as a 1:1 mixture of two epimers, is purified and separated into the two epimers by chromatography on silica gel using a 10:1 mixture of CH$_2$Cl$_2$ and methanol. There are thus obtained 33 mg (10%) of the more polar epimer (R or S)-N-[(1S,2R,3S)-1-(cyclohexylmethyl)-3-cyclopropyl-2,3-dihydroxypropyl]-8-propyl-α,6-bis(3-pyridyl)-s-triazolo[4,3-a]pyrazine-3-acetamide as yellow crystals, MS: 598 (M+H)$^+$, 76 mg (22.7%) of the pure, less polar epimer (S or R)-N-[(1S,2R,3S)-1-(cyclo-hexylmethyl)-3-cyclopropyl-2,3-dihyroxypropyl]-8-propyl-a,6-bis(3-pyridyl)-s-triazolo[4,3-a]pyrazine-3-acetamide, MS: 598 (M+H)$^+$, and 166 mg (49.6%) of a mixture of both epimers, i.e. (RS)-N-[(1S,2R,3S)-1-(cyclohexylmethyl)-3-cyclopropyl-2,3-dihydroxypropyl]-8-propyl-α,6-bis(3-pyridyl)-s-triazolo[4,3-a]pyrazine-3-acetamide, MS: 598 (M+H)$^+$.

The rac-8-propyl-6-(3-pyridyl)-α-(3-pyridylmethyl)-s-triazolo[4,3-a]pyrazine-3-acetic acid used as the starting material was prepared as follows:

3.31 g (11.7 mmol) of 3-(2-amino-1,1-diethoxyethyl)-pyridine [Org. Synthesis 64, 19(1986)] and 1.17 ml (11.7 mmol) of 2-oxo-n-valeric acid are dissolved in 150 ml of dimethylformamide, 2.63 ml (23.4 mmol) of N-methylmorpholine and 4.85 g (12.8 mmol) of TBTU [2-(1H-benzotriazol-1-yl)-1,1,3,3-tetramethyluronium tetrafluoroborate] are added thereto and the solution is stirred at room temperature under argon for 14 hours. The mixture is partitioned between ethyl acetate and water and there are obtained, after the usual working-up of the organic phase, 2.6 g of crude product as a brown oil which is purified by chromatography on silica gel (eluent: 95:5 mixture of CH$_2$Cl$_2$ and ether, yield: 1.42 g (39%) of N-[2,2-diethoxy-2-(3-pyridyl)ethyl]-2-oxovaleramide, MS: 309 (M+H)$^+$.

500 mg (1.62 mmol) of N-[2,2-diethoxy-2-(3-pyridyl)ethyl]-2-oxovaleramide are treated with 20 ml of 2N hydrochloric acid and subsequently stirred at 30° for 22 hours. Thereafter the solvent is removed in a high vacuum and the residue is treated twice with toluene, which is again removed each time under reduced pressure.

The desired product is thus obtained as beige crystals, yield: 420 mg (95%). Recrystallization from methanol/ether yields N-(nicotinoylmethyl)-2-oxo-valeramide, melting point 80°-82°.

150 mg (0.55 mmol) of N-(nicotinoylmethyl)-2-oxovaleramide and 1.5 g (19.3 mmol) of ammonium acetate are dissolved in 10 ml of ethanol and the solution is heated to reflux for 90 minutes. Then, the mixture is poured on to 50 ml of ice/water, extracted three times with 20 ml of ethyl acetate each time, the organic phase is washed with 30 ml of water, dried over sodium sulfate and the solvent is then removed under reduced pressure, crude yield: 195 mg of yellow crystals. Recrystallization from ethyl acetate yields 3-propyl-5-(3-pyridyl)-2(1H)-pyrazinedione, melting point 188°-189° (dec.).

430 mg (2 mmol) of 3-propyl-5-(3-pyridyl)-2(1H)-pyrazinedione are treated with 2 ml of phosphorus oxychloride and the mixture is subsequently heated to reflux for 5 hours. Then, the phosphorus oxychloride is removed under reduced pressure, the residue is evaporated once with toluene and the crude product is dissolved in 20 ml of $CH_2Cl_2$ and washed with 10 ml of ice-water. The aqueous phase is extracted once with 10 ml of $CH_2Cl_2$ and the combined organic phases are dried over sodium sulfate. The solvent is removed under reduced pressure and the desired 2-chloro-3-propyl-5-(3-pyridyl)pyrazine is obtained as beige crystals, yield: 468 mg (36%); melting point 207°-209° (from $CH_2Cl_2$/ether).

2.5 ml of pyridine are treated with 2.5 ml (51.4 mmol) of hydrazine hydrate, 500 mg (1.85 mmol) of 2-chloro-3-propyl-5-(3-pyridyl)pyrazine are added thereto and the mixture is subsequently heated to reflux for 90 minutes. Thereafter, the reaction solution is left to cool, 10 ml of water are added, the mixture is cooled at 5° for 30 minutes and finally the crystallized-out product is filtered off under suction.

The crude product is dried over potassium hydroxide at 40° under reduced pressure and recrystallized from alcohol/water (1:1), whereby there are obtained 270 mg (63.6%) of 2-hydrazino-3-propyl-5-(3-pyridyl)pyrazine as beige needles, melting point 162°-163°.

340 mg (1.35 mmol) of diethyl (3-pyridyl)malonate (Arch. Pharm. 308, (1975) 663), 311 mg (1.35 mmol) of 2-hydrazino-3-propyl-5-(3-pyridyl)pyrazine and 257 mg (1.35 mmol) of p-toluenesulphonic acid are treated with 150 ml of xylene and the mixture is subsequently heated to reflux on a water separator for 12 hours. Thereafter, the xylene is distilled off, the residue is dissolved in $CH_2Cl_2$, washed with sodium bicarbonate solution, the organic phase is dried over sodium sulfate and the solvent is removed under reduced pressure. The residue is chromatographed on silica gel using a 10:1 mixture of $CH_2Cl_2$ and methanol, whereby there are obtained 300 mg (53%) of ethyl rac-8-propyl-6-(3-pyridyl)-α-(3-pyridyl-methyl)-s-triazolo[4,3-a]pyrazine-3-acetate, MS: 416 (M)+.

300 mg (0.72 mmol) of ethyl rac-8-propyl-6-(3-pyridyl)-α-(3-pyridylmethyl)-s-triazolo[4,3-a]pyrazine-3-acetate are dissolved in 50 ml of ethanol, treated with 1.44 ml of 1N sodium hydroxide solution (1.44 mmol) and the solution is subsequently heated at 50° for 2 hours. It is neutralized by adding 1.44 ml of 1N hydrochloric acid (pH 5) and evaporated to dryness under reduced pressure. The residue is then partitioned between water (5 ml) and a 10:1 mixture of $CH_2Cl_2$ and methanol (50 ml). The organic phase is dried over sodium sulfate and the solvent is removed under reduced pressure. There are thus obtained 300 mg (53%) of rac-8-propyl-6-(3-pyridyl)-α-(3-pyridylmethyl)-s-triazolo[4,3-a]pyrazine-3-acetic acid as a yellow amorphous powder, $R_F$:0.1 ($CH_2Cl_2$/MeOH; 5:1).

EXAMPLE 2

The following compounds were prepared in a manner analogous to that described in Example 1:

From rac-α-(imidazol-4-ylmethyl)-8-propyl-6-(3-pyridyl)-s-triazolo[4,3-a]pyrazine-3-acetic acid and (1S,2R,3S)-3-amino-4-cyclohexyl-1-cyclopropyl-1,2-butanediol there are obtained two epimers (R or S)-N-[(1S,2R,3S)-1-(cyclohexylmethyl)-3-cyclopropyl-2,3-dihydroxypropyl]-α-(imidazol-4-ylmethyl)-8-propyl-6-(3-pyridyl)-s-triazolo[4,3-a]pyrazine-3-acetamide and (R or S)-N-[(1S,2R,3S)-1-(cyclohexylmethyl)-3-cyclopropyl-2,3-dihydroxypropyl]-α-(imidazol-4-ylmethyl)-8-propyl-6-(3-pyridyl)-s-triazolo[4,3-a]pyrazine-3-acetamide, each as a pale yellow solid, MS: 587 (M+H)+;

from 8-propyl-6-(3-pyridyl)-s-triazolo[4,3-a]pyrazine-3-acetic acid and (1S,2R,3S)-3-amino-4-cyclohexyl-1-cyclopropyl-1,2-butanediol there is obtained N-[(1S,2R,3S)-1-(cyclohexylmethyl)-3-cyclopropyl-2,3-dihydroxypropyl]-8-propyl-6-(3-pyridyl)-s-triazolo[4,3-a]pyrazine-3-acetamide as a solid, MS: 507 (M+H)+;

from rac-8-isopropyl-6-(3-pyridyl)-α-(3-pyridylmethyl)-s-triazolo[4,3-a]pyrazine-3-acetic acid and (1S,2R,3S)-3-amino-4-cyclohexyl-1-cyclopropyl-1,2-butanediol there is obtained (RS)-N-[(1S,2R,3S)-1-(cyclohexylmethyl)-3-cyclopropyl-2,3-dihydroxypropyl]-8-isopropyl-6-(3-pyridyl)-α-(3-pyridylmethyl)-s-triazolo[4,3-a]pyrazine-3-acetamide as a 1:1 epimer mixture, MS: 598 (M+H)+;

from rac-8-isopropyl-α-(imidazol-1-ylmethyl)-6-(3-pyridyl)-s-triazolo[4,3-a]pyrazine-3-acetic acid and (1S,2R,3S)-3-amino-4-cyclohexyl-1-cyclopropyl-1,2-butanediol there are obtained the two epimers (S or R)-N-[(1S,2R,3S)-1-(cyclohexylmethyl)-3-cyclopropyl-2,3-dihydroxypropyl]-8-isopropyl-α-(imidazol-4-ylmethyl)-6-(3-pyridyl)-s-triazolo[4,3-a]-pyrazine-3-acetamide and (R or S)-N-[(1S,2R,3S)-1-(cyclohexylmethyl)-3-cyclopropyl-2,3-dihydroxypropyl]-8-isopropyl-α-(imidazol-4-ylmethyl)-6-(3-pyridyl)-s-triazolo[4,3-a]-pyrazine-3-acetamide, each as a pale yellow solid, MS: 587 (M+H)+;

from rac-8-isobutyl-6-(3-pyridyl)-α-(3-pyridylmethyl)-s-triazolo[4,3-a]pyrazine-3-acetic acid and (1S,2R,3S)-3-amino-4-cyclohexyl-1-cyclopropyl-1,2-butanediol there is obtained the 3:1-epimer mixture (RS)-N-[(1S,2R,3S)-1-(cyclohexylmethyl)-3-cyclopropyl-2,3-dihydroxypropyl]-8-isobutyl-α-(3-pyridylmethyl)-6-(3-pyridyl)-s-triazolo[4,3-a]pyrazine-3-acetamide and the less polar, pure epimer (S or R)-N-[(1S,2R,3S)-1-(cyclohexylmethyl)-3-cyclopropyl-2,3-di-hydroxypropyl]-8-isobutyl-α-(3-pyridylmethyl)-6-(3-pyridyl)-s-triazolo[4,3-a]pyrazine-3-acetamide, each as a pale yellow solid, MS: 612 (M+H)+;

from rac-8-isobutyl-α-(imidazol-1-ylmethyl)-6-(3-pyridyl)-s-triazolo[4,3-a]pyrazine-3-acetic acid and (1S,2R,3S)-3-amino-4-cyclohexyl-1-cyclopropyl-1,2-butanediol there are obtained the two epimers (S or R)-N-[(1S,2R,3S)-1-(cyclohexylmethyl)-3-cyclohexyl-2,3-dihydroxypropyl]-α-(imidazol-4-ylmethyl)-8-isobutyl-6-(3-pyridyl)-s-triazolo[4,3-a]pyra-zine-3-acetate and (R or S)-N-[(1S,2R,3S)-1-(cyclohexylmethyl)-3-cyclohexyl-2,3-dihydroxypropyl]-α-(imidazol-4-ylmethyl)-8-isobutyl-6-(3-pyridyl)-s-triazolo[4,3-a]pyrazine-3-acetate, each as a solid, MS: 601 (M+H)+;

from 8-isobutyl-6-(3-pyridyl)-s-triazolo[4,3-a]pyrazine-3-acetic acid and (1S,2R,3S)-3-amino-4-cyclohexyl-1-cyclopropyl-1,2-butanediol there is obtained N-[(1S,2R,3S)-1-(cyclohexylmethyl)-3-cyclopropyl-2,3-dihydroxypropyl]-8-isobutyl-6-(3-pyridyl)-s-triazolo[4,3-a]pyrazine-3-acetamide as a solid, MS: 521 (M+H)+;

from rac-6-(4-pyridyl)-α-(3-pyridylmethyl)-8-propyl-s-triazolo[4,3-a]pyrazine-3-acetic acid and (1S,2R,3S)-3-amino-4-cyclohexyl-1-cyclopropyl-1,2-butanediol there is obtained the 1:1 epimer mixture (RS)-N-[(1S,2R,3S)-1-(cyclohexylmethyl)-3-cyclopropyl-2,3-dihydroxypropyl]-8-propyl-6-(4-pyridyl)-α-(3-pyridylmethyl)-s-triazolo[4,3-a]pyrazine-3-acetamide as a solid, MS: 598 (M+H)+;

from rac-α-(imidazol-4-ylmethyl)-8-propyl-6-(4-pyridyl)-s-triazolo[4,3-a]pyrazine-3-acetic acid and (1S,2R,3S)-3-amino-4-cyclohexyl-1-cyclopropyl-1,2-butanediol there is obtained the (RS)-N-[(1S,2R,3S)-1-(cyclohexylmethyl)-3-cyclopropyl-2,3-dihydroxypropyl]-α-(imidazol-4-ylmethyl)-8-propyl-6-(4-pyridyl)-s-triazolo[4,3-a]pyrazine-3-acetamide as a 1:1 epimer mixture, MS: 587 (M+H)+;

from 8-propyl-6-(4-pyridyl)-s-triazolo[4,3-a]pyrazine-3-acetic acid and (1S,2R,3S)-3-amino-4-cyclohexyl-1-cyclopropyl-1,2-butanediol there is obtained N-[(1S,2R,3S)-1-(cyclohexylmethyl)-3-cyclopropyl-2,3-dihydroxypropyl]-8-propyl-6-(4-pyridyl)-s-triazolo[4,3-a]pyrazine-3-carboxamide as a pale yellow solid, MS: 507 (M+H)+;

from 6-phenyl-8-propyl-s-triazolo[4,3-b]pyridazine-3-acetic acid and (1S,2R,3S)-3-amino-4-cyclohexyl-1-cyclopropyl-1,2-butanediol there is obtained N-[(1S,2R,3S)-1-(cyclohexylmethyl)-3-cyclopropyl-2,3-dihydroxypropyl]-6-phenyl-8-propyl-s-triazolo[4,3-b]pyridazine-3-acetamide as a solid, MS: 508 (M+H)−;

from rac-6-phenyl-8-propyl-α-(3-pyridylmethyl)-s-triazolo[4,3-b]pyridazine-3-acetic acid and (1S,2R,3S)-3-amino-4-cyclohexyl-1-cyclopropyl-1,2-butanediol there is obtained (RS)-N-[(1S,2R,3S)-1-(cyclohexylmethyl)-3-cyclopropyl-2,3-dihydroxypropyl]-6-phenyl-8-propyl-α-(3-pyridylmethyl)-s-triazolo[4,3-b]pyridazine-3-carboxamide as a solid, MS:598 (M+H)+;

from 8-benzyl-6-phenyl-s-triazolo[4,3-b]pyridazine-3-acetic acid and (1S,2R,3S)-3-amino-4-cyclohexyl-1-cyclopropyl-1,2-butanediol there is obtained 8-benzyl-N-[(1S,2R,3S)-1-(cyclohexylmethyl)-3-cyclopropyl-2,3-dihydroxypropyl]-6-phenyl-s-triazolo[4,3-b]pyridazine-3-acetamide, MS: 482 (M-C4H7O)+;

from (RS)-8-benzyl-6-phenyl-α-(3-pyridylmethyl)-s-triazolo[4,3-b]pyridazine-3-acetic acid and (1S,2R,3S)-3-amino-4-cyclohexyl-1-cyclopropyl-1,2-butanediol there is obtained (RS)-8-benzyl-N-[(1S,2R,3S)-1-(cyclohexylmethyl)-3-cyclopropyl-2,3-dihydroxypropyl]-6-phenyl-α-(3-pyridylmethyl)-s-triazolo[4,3-b]pyridazine-3-acetamide, MS: 645 (M+H)+;

from rac-8-propyl-6-(3-pyridyl)-α-(3-pyridylmethyl)-s-triazolo[4,3-a]pyrazine-3-acetic acid and (2S,3R,4S)-2-amino-1-cyclohexyl-6-methyl-3,4-heptanediol (J. Med. Chem. 31 (12), 2277, 1988) there are obtained the two epimers (S or R)-N-[(1S,2R,3S)-1-(cyclohexylmethyl)-2,3-dihydroxy-5-methylhexyl]-8-propyl-6-(3-pyridyl)-α-(3-pyridylmethyl)-s-triazolo[4,3-a]pyrazine-3-acetamide and (R or S)-N-[(1S,2R,3S)-1-(cyclohexylmethyl)-2,3-dihydroxy-5-methylhexyl]-8-propyl-6-(3-pyridyl)-α-(3-pyridylmethyl)-s-triazolo[4,3-a]pyrazine-3-acetamide, MS: in each case 614 (M+H)+;

from rac-8-propyl-6-(3-pyridyl)-α-(3-pyridylmethyl)-s-triazolo[4,3-a]pyrazine-3-acetic acid and (1S,2R,3S)-3-amino-1-cyclopropyl-4-phenyl-1,2-butanediol there is obtained the 1:1 epimer mixture (RS)-N-[(1S,2R,3S)-1-(cyclohexylmethyl)-3-cyclopropyl-2,3-dihydroxypropyl]-8-propyl-α-(3-pyridylmethyl)-6-(3-pyridyl)-s-triazolo[4,3-a]pyrazine-3-acetamide, MS: 592 (M+H)+;

from rac-8-benzyl-6-(3-pyridyl)-α-(3-pyridylmethyl)-s-triazolo[4,3-a]pyrazine-3-acetic acid and (1S,2R,3S)-3-amino-4-cyclohexyl-1-cyclopropyl-1,2-butanediol there is obtained the 1:1 epimer mixture (RS)-8-benzyl-N-[(1S,2R,3S)-1-(cyclohexylmethyl)-3-cyclopropyl-2,3-dihydroxypropyl]-6-(3-pyridyl)-α-(3-pyridylmethyl)-s-triazolo[4,3-a]-pyrazine-3-acetamide, MS: 646 (M+H)+;

from rac-8-benzyl-α-(imidazol-4-ylmethyl)-6-(3-pyridyl)-s-triazolo[4,3-a]pyrazine-3-acetic acid and (1S,2R,3S)-3-amino-4-cyclohexyl-1-cyclopropyl-1,2-butanediol there is obtained the 1:1 epimer mixture (RS)-8-benzyl-N-[(1S,2R,3S)-1-(cyclohexylmethyl)-3-cyclopropyl-2,3-dihydroxypropyl]-α-(imidazol-4-ylmethyl)-6-(3-pyridyl)-s-triazolo[4,3-a]-pyrazine-3-acetamide, MS: 635 (M+H)+;

from 8-benzyl-6-(3-pyridyl)-s-triazolo[4,3-a]pyrazine-3-acetic acid and (1S,2R,3S)-3-amino-4-cyclohexyl-1-cyclopropyl-1,2-butanediol there is obtained 8-benzyl-N-[(1S,2R,3S)-1-(cyclohexylmethyl)-3-cyclopropyl-2,3-dihydroxypropyl]-6-(3-pyridyl)-s-triazolo[4,3-a]pyrazine-3-acetamide as a solid, MS: 555 (M+H)+;

from rac-8-propyl-6-(3-pyridyl)-α-(3-pyridylmethyl)-s-triazolo[4,3-a]pyrazine-3-acetic acid and (2S,3R,4S)-2-amino-1-cyclohexyl-5-methyl-3,4-hexanediol (EP-A 0.332.008) there are obtained the two epimers (R or S)-N-[(1S,2R,3S)-1-(cyclohexylmethyl)-2,3-dihydroxy-4-methylpentyl]-8-oxopropyl-6-(3-pyridyl)-α-(3-pyridylmethyl)-s-triazolo-[4,3-a]pyrazine-3-acetamide and (S or R)-N-[(1S,2R,3S)-1-(cyclohexylmethyl)-2,3-dihydroxy-4-methylpentyl]-8-oxopropyl-6-(3-pyridyl)-α-(3-pyridylmethyl)-s-triazolo[4,3-a]pyrazine-3-acetamide, MS: in each case 600 (M+H)+;

from rac-α-(imidazol-4-ylmethyl)-8-propyl-6-(3-pyridyl)-s-triazolo[4,3-a]pyrazine-3-acetic acid and (1S,2R,3S)-3-amino-1-cyclopropyl-4-phenyl-1,2-butanediol there is obtained the 2:1 epimer mixture (RS)-N-[(1S,2R,3S)-1-(cyclohexylmethyl)-3-cyclopropyl-2,3-dihydroxypropyl]-α-(imidazol-4-ylmethyl)-8-propyl-6-(3-pyridyl)-s-triazolo[4,3-a]pyrazine-3-acetamide as a solid, MS: 580 (M)+;

from rac-α-(imidazol-4-ylmethyl)-8-propyl-6-(3-pyridyl)-s-triazolo[4,3-a]pyrazine-3-acetic acid and (2S,3R,4S)-2-amino-1-cyclohexyl-6-methyl-3,4-heptanediol there are obtained the two epimers (R or S)-N-[(1S,2R,3S)-1-(cyclohexylmethyl)-2,3-dihydroxy-4-methylhexyl]-α-(imidazol-4-ylmethyl)-8-propyl-6-(3-pyridyl)-s-triazolo[4,3-a]pyrazine-3-acetamide and (S or R)-N-[(1S,2R,3S)-1-(cyclohexylmethyl)-2,3-dihydroxy-4-methylhexyl]-α-(imidazol-4-yl-methyl)-8-propyl-6-(3-pyridyl)-s-triazolo[4,3-a]pyrazine-3-acetamide, MS: in each case 603 (M+H)+;

from rac-α-(imidazol-4-ylmethyl)-8-propyl-6-(3-pyridyl)-s-triazolo[4,3-a]pyrazine-3-acetic acid and (2S,3R,4S)-2-amino-1-cyclohexyl-5-methyl-3,4-hexanediol there are obtained the two epimers (R or S)-N-[(1S,2R,3S)-1-(cyclohexylmethyl)-2,3-dihydroxy-4-methylpentyl]-α-(imidazol-4-ylmethyl)-8-propyl-6-(3-pyridyl)-s-triazolo[4,3-a]pyrazine-3-acetamide and (S or R)-N-[(1S,2R,3S)-1-(cyclohexylmethyl)-2,3-dihydroxy-4-methylpentyl]-α-(imidazol-4-ylmethyl)-8-propyl-6-(3- pyridyl)-s-triazolo[4,3-a]pyrazine-3-acetamide, MS: in each case 589 (M+H)+;

from rac-8-propyl-α-(3-pyridylmethyl)-6-(3-pyridyl)-s-triazolo[4,3-b]pyridazine-3-acetic acid and (1S,2R,3S)-3-amino-4-cyclohexyl-1-cyclopropyl-1,2-butanediol there is obtained (RS)-N-[(1S,2R,3S)-1-(cyclohexylmethyl)-3-cyclopropyl-2,3-dihydroxypropyl]-8-propyl-α-(3-pyridylmethyl)-6-(3-pyridyl)-s-triazolo[4,3-b]pyridazine-3-acetamide as a 1:1 epimer mixture, MS: 598 (M+H)+;

from rac-8-propyl-α-(3-pyridylmethyl)-6-(2-thienyl)-s-triazolo[4,3-b]pyridazine-3-acetic acid and (1S,2R,3S)-3-amino-4-cyclohexyl-1-cyclopropyl-1,2-butanediol there are obtained the two epimers (S or R)-N-[(1S,2R,3S)-1-(cyclohexylmethyl)-3-cyclopropyl-2,3-dihydroxypropyl]-8-propyl-α-(3-pyridylmethyl)-6-(2-thienyl)-s-triazolo[4,3-b]pyridazine-3-acetamide and (R or S)-N-[(1S,2R,3S)-1-(cyclohexylmethyl)-3-cyclopropyl-2,3-dihydroxypropyl]-8-propyl-α-(3-pyridylmethyl)-6-(2-thienyl)-s-triazolo[4,3-b]pyridazine-3-acetamide, each as a solid, MS: 603 (M+H)+;

from 8-propyl-6-(2-thienyl)-s-triazolo[4,3-b]-pyridazine-3-acetic acid and (1S,2R,3S)-3-amino-4-cyclohexyl-1-cyclopropyl-1,2-butanediol there is obtained N-[(1S,2R,3S)-1-(cyclohexylmethyl)-3-cyclopropyl-2,3-dihydroxypropyl]-8-propyl-6-(2-thienyl)-s-triazolo[4,3-b]pyridazine-3-acetamide as a solid, MS: 511 (M)+;

from rac-8-propyl-6-(3-pyridyl)-α-(3-pyridylmethyl)-s-triazolo[4,3-a]pyrazine-3-acetic acid and (1R or S,2R or S)-1-[(1R,2S)-1-amino-3-cyclohexyl-1-hydroxypropyl]-1,2-cyclohexanediol there are obtained the two epimers (R or S)-N-[(1S,2R)-1-(cyclohexylmethyl)-2-hydroxy-2-[(1R or S,2R or S)-1,2-dihydroxyphenyl]ethyl]-8-propyl-α-(3-pyridylmethyl)-8-propyl-s-triazolo[4,3-a]pyrazine-3-acetamide and (S or R)-N-[(1S,2R)-1-(cyclohexylmethyl)-2-hydroxy-2-[(1R or S,2R or S)-1,2-dihydroxyphenyl]ethyl]-8-propyl-α-(3-pyridylmethyl)-8-propyl-s-triazolo[4,3-a]pyrazine-3-acetamide, each as a solid, MS: 642 (M+H)+;

from (RS)-8-[(RS)-1-methylpropyl]-α-(3-pyridylmethyl)-6-(3-pyridyl)-s-triazolo[4,3-a]pyrazine-3-acetic acid and (1S,2R,3S)-3-amino-4-cyclohexyl-1-cyclopropyl-1,2-butanediol there are obtained the two epimer mixtures (S or R)-N-[(1S,2R,3S)-1-(cyclohexylmethyl)-3-cyclopropyl-2,3-dihydroxypropyl]-8-[(RS)-1-methylpropyl]-α-(3-pyridylmethyl)-6-(3-pyridyl)-s-triazolo[4,3-a]pyrazine-3-acetamide and (RS)-N-[(1S,2R,3S)-1-(cyclohexylmethyl)-3-cyclopropyl-2,3-dihydroxypropyl]-8-[(RS)-1-methylpropyl]-α-(3-pyridylmethyl)-6-(3-pyridyl)-s-triazolo[4,3-a]pyrazine-3-acetamide, each as a pale yellow solid, MS: 612 (M+H)+;

from rac-8-(1-methylpropyl)-6-(3-pyridyl)-s-triazolo[4,3-a]pyrazine-3-acetic acid and (1S,2R,3S)-3-amino-4-cyclohexyl-1-cyclopropyl-1,2-butanediol there is obtained N-[(1S,2R,3S)-1-(cyclohexylmethyl)-3-cyclopropyl-2,3-dihydroxypropyl]-8-[(RS)-1-methylpropyl]-6-(3-pyridyl)-s-triazolo[4,3-a]pyrazine-3-carboxamide as a solid, MS: 520, (M)+, from rac-α-(imidazol-4-ylmethyl)-8-[(RS)-1-methylpropyl]-6-(3-pyridyl)-s-triazolo[4,3-a]pyrazine-3-acetic acid and (1S,2R,3S)-3-amino-4-cyclohexyl-1-cyclopropyl-1,2-butanediol there are obtained the two 1:1 epimer mixtures (S or R)-8-[(RS)-1-methylpropyl]-N-[(1S,2R,3S)-1-(cyclohexylmethyl)-3-cyclopropyl-2,3-dihydroxypropyl]-α-(imidazol-4-yl-methyl)-6-(3-pyridyl)-s-triazolo[4,3-a]pyrazine-3-acetamide and (R or S)-8-[(RS)-1-methylpropyl]-N-[(1S,2R,3S)-1-(cyclohexylmethyl)-3-cyclopropyl-2,3-dihydroxypropyl]-α-(imidazol-4-ylmethyl)-6-(3-pyridyl)-s-triazolo[4,3-a]pyrazine-3-acetamide, each as a pale yellow solid, MS: 601 (M+H)+;

from rac-α-methyl-8-propyl-6-(3-pyridyl)-s-triazolo[4,3-a]pyrazine-3-acetic acid and (1S,2R,3S)-3-amino-4-cyclohexyl-1-cyclopropyl-1,2-butanediol there is obtained (RS)-N-[(1S,2R,3S)-1-(cyclohexylmethyl)-3-cyclopropyl-2,3-dihydroxypropyl]-α-methyl-8-propyl-6-(3-pyridyl)-s-triazolo[4,3-a]pyrazine-3-acetamide as a 1:1 epimer mixture, MS: 521 (M+H)+; and from rac-α-methyl-8-[(RS)-1-methylpropyl]-6-(3-pyridyl)-s-triazolo[4,3-a]pyrazine-3-acetic acid and (1S,2R,3S)-3-amino-4-cyclohexyl-1-cyclopropyl-1,2-butanediol there is obtained (RS)-8-[(RS)-1-methylpropyl]-N-[(1S,2R,3S)-1-(cyclohexylmethyl)-3-cyclopropyl-2,3-dihydroxypropyl]-α-methyl-6-(3-pyridyl)-s-triazolo[4,3-a]pyrazine-3-acetamide as a mixture of diastereomers, MS: 535 (M+H)+.

The acids and amine diols used as the starting materials were prepared as follows:

rac-α-(Imidazol-4-ylmethyl)-8-propyl-6-(3-pyridyl)-s-triazolo[4,3-a]pyrazine-3-acetic acid In a manner analogous to that described in Example 1, by condensing 2-hydrazino-3-propyl-5-(3-pyridyl)-pyrazine with diethyl (imidazol-4-yl-methyl)malonate (J.Chem.Soc. 99, (1911) 1390) there is obtained ethyl rac-α-(imidazol-4-ylmethyl)-8-propyl-6-(3-pyridyl)-s-triazolo[4,3-a]pyrazine-3-acetate, MS: 405 (M)+, which is converted into the above acid by saponification analogously to Example 1.

8-Propyl-6-(3-pyridyl)-s-triazolo[4,3-a]pyrazine-3-acetic acid

In a manner analogous to that described in Example 1, by condensing 2-hydrazino-3-propyl-5-(3-pyridyl)-pyrazine with diethyl malonate in toluene in place of xylene there is obtained ethyl 8-propyl-6-(3-pyridyl)-s-triazolo[4,3-a]pyrazine-3-acetate, MS: 325 (M)+, and by corresponding basic saponification there is obtained the desired acid, MS: 269 (M-$C_2H_4$)+.

rac-8-Isopropyl-6-(3-pyridyl)-α-(3-pyridylmethyl)-s-triazolo[4,3-a]pyrazine-3-acetic acid In a manner analogous to Example 1, by condensing 3-(2-amino-1,1-diethoxyethyl)pyridine with 3-methyl-2-oxo-butanoic acid there is obtained N-[2,2-diethoxy-2-(3-pyridyl)ethyl]-3,3-dimethyl-2-oxobutyramide. Acidic hydrolysis to 3-methyl-N-(nicotinoylmethyl)-2-oxobutyramide and subsequent ring closure gives 3-isopropyl-5-(3-pyridyl)-2(1H)-pyrazinone as a yellow, crystalline solid, melting point 200°-202° (from ethyl acetate). The conversion into the corresponding chloride, 2-chloro-3-isopropyl-5-(3-pyridyl)pyrazine, is effected analogously to Example 1.

Hydrazinolysis yields 2-hydrazino-3-isopropyl-5-(3-pyridyl)pyrazine as beige crystals, melting point 164°-165° (from ethanol/water), and subsequent condensation with diethyl (3-pyridyl)malonate yields ethyl rac-8-isopropyl-6-(3-pyridyl)-α-(3-pyridylmethyl)-s-triazolo-[4,3-a]pyrazine-3-acetate as a pale yellow solid, MS: 416 (M)+, which is converted into the above acid by basic saponification.

rac-8-Isopropyl-α-(imidazol-4-ylmethyl)-6-(3-pyridyl)-s-triazolo-[4,3-a]pyrazine-3-acetic acid In a manner analogous to Example 1, by condensing 2-hydrazino-3-isopropyl-5-(3-pyridyl)pyrazine with diethyl (imidazol-4-ylmethyl)malonate there is obtained ethyl rac-8-isopropyl-α-(imidazol-4-ylmethyl)-6-(3-pyridyl)-s-triazolo[4,3-a]pyrazine-3-acetate, MS: 405 (M)+, which is converted into the above acid by alkaline saponification.

rac-8-Isobutyl-α-(3-pyridylmethyl)-6-(3-pyridyl)-s-triazolo[4,3-a]pyrazine-3-acetic acid In a manner analogous to Example 1, by condensing 3-(2-amino-1,1-diethoxyethyl)pyridine with 4-methyl-2-oxo-pentanoic acid there is obtained N-(2,2-diethoxy-2-(3-pyridyl)ethyl]-4-methyl2-oxovaleramide as a colorless, amorphous solid. Acidic hydrolysis yields 4-methyl-N-(nicotinoylmethyl)-2-oxovaleramide and subsequent ring closure yields 3-isobutyl-5-(3-pyridyl)-2(1H)-pyrazinone as a crystalline solid, melting point 195°-196° (from ethyl acetate). The conversion into the corresponding chloride, 2-chloro-3-isobutyl-5-(3-pyridyl)pyrazine, is also effected analogously to Example 1.

Hydrazinolysis of the chloride yields 2-hydrazino-isobutyl-5-(3-pyridyl)pyrazine as beige crystals, melting point 154°-155° (from ethanol/water) and subsequent condensation with diethyl (3-pyridyl)malonate yields ethyl rac-8-isobutyl-α-(3-pyridylmethyl)-6-(3-pyridyl)-s-triazolo[4,3-a]pyrazine-3-acetate, MS: 430 (M)+, which is converted into the above acid by basic saponification.

rac-α-(Imidazol-4-ylmethyl)-8-isobutyl-6-(3-pyridyl)-s-triazolo[4,3-a]pyrazine-3-acetic acid In a manner analogous to Example 1, by condensing 2-hydrazino-3-isobutyl-5-(3-pyridyl)pyrazine with diethyl (imidazol-4-ylmethyl)malonate there is obtained ethyl rac-α-(imidazol-4-ylmethyl)-8-isobutyl-6-(3-pyridyl)-s-triazolo[4,3-s]pyrazine-3-acetate, MS: 419 (M)+, which is converted into the above acid by alkaline saponification.

8-Isobutyl-6-(3-pyridyl)-s-triazolo[4,3-s]pyrazine-3-acetic acid

In a manner analogous to Example 1, by condensing 2-hydrazino-3-isobutyl-5-(3-pyridyl)pyrazine with diethyl malonate there is obtained ethyl 8-isobutyl-6-(3-pyridyl)-s-triazolo[4,3-a]pyrazine-3-acetate, MS: 339 (M)+, which is converted by saponification into the above acid: MS 267 (M-CO$_2$)+.

rac-8-Benzyl-6-(3-pyridyl)-α-(3-pyridylmethyl)-s-triazolo-[4,3-a]pyrazine-3-acetic acid In a manner analogous to Example 1, by condensing 3-(2-amino-1,1-diethoxyethyl)pyridine with phenylpyruvic acid there is obtained N-[2,2-diethoxy-2-(3-pyridyl)ethyl]-3-phenylpyruvamide as an amorphous, yellow solid. Subsequent acidic hydrolysis to 3-phenyl-N-[[(3-pyridyl)carbonyl]methyl]pyruvamide and ring closure gives 3-benzyl-5-(3-pyridyl)-2(1H)-pyrazinone as a solid, melting point 188°-190° (from ethyl acetate). Chlorination to 2-benzyl-3-chloro-6-(3-pyridyl)pyrazine and hydrazinolysis yields 2-benzyl-3-hydrazino-6-(3-pyridyl)pyrazine as a beige, crystalline solid. Melting point 183°-184° (from methanol/water).

Condensation with diethyl (3-pyridyl)malonate finally gives ethyl rac-8-benzyl-α-(3-pyridylmethyl)-6-(3-pyridyl)-s-triazolo[4,3-a]pyrazine-3-acetate, MS: 464 (M)+, which is converted into the above acid by basic saponification.

rac-8-Benzyl-α-(imidazol-4-ylmethyl)-6-(3-pyridyl)-s-triazolo[4,3-a]pyrazine-3-acetic acid In a manner analogous to that described in Example 1, by condensing 2-benzyl-3-hydrazino-6-(3-pyridyl)-pyrazine with diethyl (imidazol-4-ylmethyl)malonate there is obtained ethyl rac-8-benzyl-α-(imidazol-4-ylmethyl)-6-(3-pyridyl)-s-triazolo[4,3-a]pyrazine-3-acetate, MS: 453 (M)+, which is converted into the above acid by alkaline saponification.

8-Benzyl-6-(3-pyridyl)-s-triazolo[4,3-a]pyrazine-3-acetic acid

In a manner analogous to Example 1, by condensing 2-benzyl-3-hydrazino-6-(3-pyridyl)pyrazine with diethyl malonate there is obtained ethyl 8-benzyl-6-(3-pyridyl)-s-triazolo[4,3-a]pyrazine-3-acetate, which is converted by basic saponification into the above acid, MS: 301 (M-CO$_2$)+.

rac-6-(4-Pyridyl)-α-(3-pyridyl)-8-propyl-s-triazolo[4,3-a]pyrazine-3-acetic acid In a manner analogous to Example 1, by condensing 4-(2-amino-1,1-diethoxyethyl)pyrimidine [Org. Synthesis 64, 19 (1986)] with 2-oxopentanoic acid there is obtained N-[2,2-diethoxy-2-(4-pyridyl)ethyl]-2-oxovaleramide as a white solid, melting point 95°-96°. Subsequent acidic hydrolysis to N-(isonicotinoylmethyl)-2-oxovaleramide and ring closure gives 3-propyl-5-(4-pyridyl)-2-pyrazinone as yellow crystals, melting point 237°-238° (dec.).

Chlorination to 2-chloro-3-propyl-5-(4-pyridyl)-pyrazine and hydrazinolysis yields 2-hydrazino-3-propyl-5-(4-pyridyl)pyrazine as a red, crystalline solid, melting point 216°-217° (from ethanol/water).

Condensation with diethyl (3-pyridyl)malonate analogously to Example 1 finally gives ethyl rac-6-(4-pyridyl)-α-(3-pyridyl)-8-propyl-s-triazolo[4,3-a]pyrazine-3-acetate, MS: 416 (M)+, which is converted into the above acid by basic saponification.

rac-α-(Imidazol-4-ylmethyl)-8-propyl-6-(4-pyridyl)-s-triazolo[4,3-a]pyrazine-3-acetic acid In a manner analogous to Example 1, by condensing 2-hydrazino-3-propyl-5-(4-pyridyl)pyrazine with diethyl (imidazol-4-yl-methyl)malonate there is obtained ethyl rac-α-(imidazol-4-ylmethyl)-8-propyl-6-(4-pyridyl)-s-triazolo[4,3-a]-pyrazine-3-acetate, MS: 405 (M)+, which is converted into the above acid by basic saponification.

8-Propyl-6-(4-pyridyl)-s-triazolo[4,3-a]pyrazine-3-acetic acid

In a manner analogous to Example 1, by condensing 2-hydrazino-3-propyl-5-(4-pyridyl)pyrazine with diethyl malonate there is obtained ethyl 8-propyl-6-(4-pyridyl)-s-triazolo-[4,3-a]pyrazine-3-acetate, MS: 325 (M)+, which is converted into the above acid by basic saponification.

6-Phenyl-8-propyl-s-triazolo[4,3-b]pyridazine-3-acetic acid

In a manner analogous to Example 1, by chlorinating 6-phenyl-4-propyl-3(2H)-pyridazinone [Chim. Ther. 6, 109 (1971)] there is obtained 3-chloro-6-phenyl-4-propylpyridazine, MS: 232 (M)+, which is converted by hydrazinolysis into 3-hydrazino-6-phenyl-4-propyl-pyridazine, MS: 228 (M)+. Subsequent ring condensation with diethyl malonate to ethyl 6-phenyl-8-propyl-s-triazolo[4,3-b]pyridazine-3-acetate, MS: 324 (M)+, followed by basic saponification gives the above acid as a solid, MS: 252 (M-$CO_2$)+.

rac-6-Phenyl-8-propyl-α-(3-pyridylmethyl)-s-triazolo[4,3-b]pyridazine-3-acetic acid In a manner analogous to Example 1, by condensing 3-hydrazino-6-phenyl-4-propylpyridazine with diethyl (3-pyridyl)malonate there is obtained ethyl rac-6-phenyl-8-propyl-α-(3-pyridylmethyl)-s-triazolo[4,3-b]pyridazine-3-acetate, which is converted by basic saponification into the above acid, MS: 398 (M+H)+.

8-Benzyl-6-phenyl-s-triazolo[4,3-b]pyridazine-3-acetic acid

In a manner analogous to that described in Example 1, by the ring condensation of 4-benzyl-3-hydrazino-6-phenyl-pyridazine [Indian J. Chem., 15B, 352 (1977)] with diethyl malonate there is obtained ethyl 8-benzyl-6-phenyl-s-triazolo[4,3-b]pyridazine-3-acetate, MS: 372 (M)+, which is saponified with a base to the above acid, MS: 316 (M-CO)+.

(RS)-8-Benzyl-6-phenyl-α-(3-pyridylmethyl)-s-triazolo[4,3-b]pyridazine-3-acetic acid In a analogous manner, by the ring condensation of 4-benzyl-3-hydrazino-6-phenylpyridazine with diethyl (3-pyridyl)malonate there is obtained ethyl rac-8-benzyl-6-phenyl-α-(3-pyridylmethyl)-s-triazolo[4,3-b]pyridazine-3-acetate, which is converted by basic saponification into the above acid, MS: 436 (M+H)+.

rac-8-(1-Methylpropyl)-6-(3-pyridyl)-s-triazolo[4,3-a]pyrazine-3-acetic acid In a manner analogous to Example 1, by condensing 3-(2-amino-1,1-diethoxyethyl)pyridine with 3-methyl-2-oxopentanoic acid there is obtained rac-N-[2,2-diethoxy-2-(3-pyridyl)ethyl]-3-methyl-2-oxovaleramide as an amorphous, colorless solid. Subsequent acidic hydrolysis to rac-3-methyl-2-oxo-N-[(3-pyridylcarbonyl)methyl]valeramide hydrochloride (beige, crystalline solid, melting point 158°-159°) and ring closure gives rac-3-(1-methylpropyl)-5-(3-pyridyl)-2(1H)-pyrazinone as a yellow solid, melting point 146°-148° (from acetonitrile). The conversion into rac-2-chloro-3-(1-methylpropyl)-5-(3-pyridyl)pyrazine is also effected analogously to Example 1. Hydrazinolysis to rac-2-hydrazino-3-(1-methylpropyl)-5-(3-pyridyl)pyrazine in the form of beige crystals, melting point 166°-167° (from ethanol/water) and subsequent condensation with diethyl malonate gives ethyl rac-8-(1-methylpropyl)-6-(3-pyridyl)-s-triazolo[4,3-a]pyrazine-3-acetate, MS: 335 (M)+, which is converted by saponification into the above acid, MS: 267 (M-$CO_2$)+.

(RS)-8-[(RS)-1-Methylpropyl]-α-(3-pyridylmethyl)-6-(3-pyridyl)-s-triazolo[4,3-a]pyrazine-3-acetic acid In a manner analogous to Example 1, by condensing rac-2-hydrazino-3-(1-methylpropyl)-5-(3-pyridyl)pyrazine with diethyl (3-pyridyl)malonate there is obtained ethyl (RS)-8-[(RS)-1-methylpropyl]-α-(3-pyridylmethyl)-6-(3-pyridyl)-s-triazolo[4,3-a]pyrazine-3-acetate, MS: 430 (M)+, which is converted into the above acid by alkaline saponification.

rac-α-(Imidazol-4-ylmethyl)-8-[(RS)-1-methylpropyl]-6-(3-pyridyl)-s-triazolo[4,3-a]pyrazine-3-acetic acid In a manner analogous to Example 1, by condensing rac-2-hydrazino-3-(1-methylpropyl)-5-(3-pyridyl)pyrazine with diethyl (imidazol-4-ylmethyl)malonate there is obtained ethyl (RS)-8-[(RS)-1-methylpropyl]-α-(imidazol-4-ylmethyl)-6-(3-pyridyl)-s-triazolo[4,3-a]pyrazine-3-acetate, MS: 419 (M)+, which is converted into the above acid by alkaline saponification.

8-Propyl-6-(2-thienyl)-s-triazolo[4,3-b]pyridazine-3-acetic acid 11.2 g (200 mmol) of potassium hydroxide in 75 ml of water are added at 0° dropwise to a suspension of 11.6 g (100 mmol) of 2-oxo-n-valeric acid and 12.6 g (100 mmol) of 2-acetylthiophene in 75 ml of ethanol and the suspension is held at 0° for 48 hours. After evaporation of the ethanol the residue is made acidic with 25% hydrochloric acid and extracted three times with ethyl acetate. The combined ethyl acetate extracts are dried, filtered and evaporated. After chromatography on silica gel using a 5:1 mixture of methylene chloride and methanol as the eluent and crystallisation from ether there are obtained 10.0 g (41%) of rac-α-hydroxy-α-propyl-γ-oxo-2-thiophenebutyric acid as a colorless powder, melting point 128°-131°, MS: 197 (M-COOH)+.

A solution of 10 g of rac-α-hydroxy-α-propyl-γ-oxo-2-thiophenebutyric acid and 25 ml of hydrazine hydrate in 250 ml of ethanol is heated to reflux for 3 hours. The solution is evaporated to about 40 ml and the separated crystals are filtered off under suction. There are thus obtained 5.1 g (56%) of 4-propyl-6-(2-thienyl)-3(2H)-pyridazinone as a colorless powder. Melting point 171°-174°, MS: 220 (M)+.

Chlorination to 3-chloro-4-propyl-6-(2-thienyl)-pyridazine, MS: 238 (M)+, and hydrazinolysis yields 3-hydrazino-4-propyl-6-(2-thienyl) pyridazine, melting point 129°-132°, analogously to Example 1.

Subsequent ring condensation with diethyl malonate yields ethyl 8-propyl-6-(2-thienyl)-s-triazolo[4,3-b]pyridazin-3-acetate, which is converted by basic saponification into the desired 8-propyl-6-(2-thienyl)-s-triazolo[4,3-b]pyridazine-3-acetic acid, MS: 258 (M-$CO_2$)+.

rac-8-Propyl-α-(3-pyridylmethyl)-6-(2-thienyl)-s-triazolo-[4,3-b]pyridazine-3-acetic acid In a manner analogous to Example 1, by condensing the above-described 3-hydrazino-4-propyl-6-(2-thienyl)pyridazine with diethyl (3-pyridyl)malonate there is obtained ethyl rac-8-propyl-α-(3-pyridylmethyl)-6-(2-thienyl)-s-triazolo-[4,3-b]pyridazine-3-acetate, which is converted by alkaline saponification into the above acid, MS: 349 (M-$CO_2$)+.

rac-8-Propyl-α-(3-pyridylmethyl)-6-(3-pyridyl)-s-triazolo-[4,3-b]pyridazine-3-acetic acid In a manner analogous to that described above, by an aldol condensation of 2-oxo-n-valeric acid with 3-acetylpyridine there is obtained γ-oxo-α-[(E)-propylidene]-3-pyridinebutyric acid, MS: 219 (M+H)+. Ring closure with hydrazine yields 4-propyl-6-(3-pyridyl)-3(2H)-pyridazinone, MS: 215 (M)+, which is converted into the corresponding chloride, 3-chloro-4-propyl-6-(3-pyridyl)pyridazine, MS: 233 (M)+. Hydrazinolysis to 3-hydrazino-4-propyl-6-(3-pyridyl)pyridazine, MS: 229 (M)+, and condensation with diethyl (3-pyridyl)malonate yields ethyl rac-8-propyl-α-(3-pyridylmethyl)-6-(3-pyridyl)-s-triazolo[4,3-b]pyridazine-3-acetate, which is converted by basic saponification into the above acid, MS: 388 (M)+.

rac-α-Methyl-8-propyl-6-(3-pyridyl)-s-triazolo[4,3-a]pyrazine-3-acetic acid

In a manner analogous to that described in Example 1, by condensing 2-hydrazino-3-propyl-5-(3-pyridyl)-pyrazine with diethyl methylmalonate there is obtained ethyl rac-α-methyl-8-propyl-6-(3-pyridyl)-s-triazolo[4,3-a]pyrazine-3-acetate, MS: 339 (M)+, which by saponification analogously to Example 1 is converted into the above acid which is used directly in the next step.

rac-α-Methyl-8-[(RS)-1-methylpropyl]-6-(3pyridyl)-s-triazolo[4,3-a]pyrazine-3-acetic acid In a manner analogous to that described in Example 1, by condensing 2-hydrazino-3-[(RS)-1-methylpropyl]-5-(3-pyridyl)pyrazine with diethyl methylmalonate there is obtained ethyl rac-α-methyl-8-[(RS)-1-methyl-propyl]-6-(3-pyridyl)-s-triazolo[4,3-a]pyrazine-3-acetate, MS: 353 (M)+, which by saponification analogously to Example 1 is converted into the above acid which is used directly in the next step.

(1S,2R,3S)-3-Amino-1-cyclopropyl-4-phenyl-1,2-butanediol 9.96 ml (124.5 mmol) of bromocyclopropane in ether (100 ml) are added dropwise within 30 minutes under slight reflux to 3.03 g (124.5 mmol) of magnesium in absolute ether (10 ml) and the mixture is subsequently heated to reflux for 2½ hours. Subsequently, 6.25 g (22.63 mmol) of tert.-butyl [1S,2R)-1-benzyl-2-cyano-2-hydroxyethyl]carbamate (EP-A 0.266.950) are added dropwise within 45 minutes under reflux and the mixture is heated at reflux for a further 2½ hours. The mixture is then left to cool to 10°, 10% citric acid (100 ml) is added dropwise thereto and the mixture is extracted twice with 250 ml of ether each time. After usual working-up of the organic phase the crude product is purified by flash chromatography on silica gel using a 9:1 mixture of toluene and ethyl acetate as the eluent. In this manner there are obtained 2.83 g (39%) of tert.-butyl [(1S,2R)-1-benzyl-2-(cyclopropylcarbonyl)-2-hydroxyethyl]carbamate, MS:246 (M-C₃H₉O)+.

2.83 g (8.77 mmol) of tert.-butyl [(1S,2R)-1-benzyl-2-(cyclopropylcarbonyl)-2-hydroxyethyl]carbamate are dissolved in methylene chloride (130 ml), acetic acid (3 ml) is added thereto and the mixture is then treated portionwise at 0°-10° with 332 mg (8.78 mmol) of sodium borohydride. The reaction solution is stirred at 5° for a further 2 hours and then partitioned between 2N sodium bicarbonate solution and methylene chloride. After the usual working-up of the organic phase the residue is crystallized from ether/hexane, whereby there are obtained 2.1 g (74%) of tert-butyl [(1S,2R,3S)-1-(cyclohexylmethyl)-3-cyclopropyl-2,3-dihydroxy-propyl]carbamate, melting point 83°-85°.

2.0 g (6.23 mmol) of tert-butyl [(1S,2R,3S)-1-(cyclohexylmethyl)-3-cyclopropyl-2,3-dihydroxypropyl]-carbamate are dissolved in methanol (20 ml), 2N hydrochloric acid (20 ml) is added thereto and the solution is heated to 50° for 90 minutes.

The solution is neutralized by adding 1N sodium hydroxide solution (40 ml) and concentrated to dryness under reduced pressure. The residue is partitioned between water and methylene chloride and the organic phase is worked-up as usual. There is thus obtained the desired (1S,2R,3S)-3-amino-1-cyclopropyl-4-phenyl-1,2-butanediol as a white, crystalline solid, yield 0.7 g (50.8%), MS: 150 (M-C₄H₈O)+.

(1R or S,2R or S)-1-[(1R,2S)-1-Amino-3-cyclohexyl-1-hydroxy-propyl]-1,2-cyclohexanediol 1.28 g (5 mmol) of tert-butyl (1S)-(2-cyclohexyl-1-formylethyl))carbamate (EP-A 0.332.008) are dissolved in 25 ml of ether and there are added dropwise thereto at −78° 70 ml (7 molar eq.) of a 0.5 molar 1-lithium-1-cyclohexene solution (J.C.S. 1950, 2014) in ether. Thereafter, the reaction solution is left to react at −78° for 1½ hours and is subsequently heated to reflux for a further 48 hours. After the usual aqueous working-up the desired product is obtained as an epimer mixture which is separated into the individual components by chromatography on silica gel (eluent: 9:1 mixture of toluene and ethyl acetate). In this manner there are obtained 270 mg (16%) of tert-butyl [(1S,2S)-2-(1-cyclohexen-1-yl)-1-(cyclohexylmethyl)ethyl]carbamate as crystals and 800 mg (47%) of tert-butyl [(1S,2R)-2-(1-cyclohexen-1-yl)-1-(cyclohexylmethyl)ethyl]carbamate as an oil, R_F:0.4 and, respectively, 0.35 (4:1 mixture of toluene and ethyl acetate as the eluent).

260 mg of tert-butyl [(1S,2S)-2-(1-cyclohexen-1-yl)-1-(cyclohexylmethyl)ethyl]carbamate (or the epimeric tert-butyl [(1S,2R)-2-(1-cyclohexen-1-yl)-1-(cyclohexylmethyl)ethyl]-carbamate) are dissolved in 2,2-dimethoxypropane (10 ml), 15 mg of p-toluenesulphonic acid monohydrate are added thereto and the solution is stirred at room temperature for 3 hours. After the usual aqueous working-up the residue is chromatographed on silica gel (ethyl acetate/toluene; 9:1) and there are obtained 270 mg (39%) of tert-butyl (4S,5S)-5-(1-cyclohexen-1-yl)-4-(cycloheylmethyl)-2,2-dimethyl-3-oxazolidinecarboxylate, as an oil, R_F: 0.4 (9:1 mixture of ethyl acetate and toluene as the eluent).

340 mg (0.9 mmol) of tert-butyl (4S,5S)-5-(1-cyclohexen-1-yl)-4-(cycloheylmethyl)-2,2-dimethyl-3-oxazolidinecarboxylate in 36 ml of a 3:1 mixture of acetone and water are treated with 2.27 mmol of 4-methylmorpholine 4-oxide monohydrate and subsequently with 3.4 ml of osmium tetroxide solution (1 g of osmium tetroxide in 199 ml of t-butanol and 1 ml of t-butyl hydroperoxide, 70% in water) and the solution is stirred at room temperature for 4 hours. Subsequently, it is treated with 3.4 ml of 38% sodium bisulphite solution, concentrated under reduced pressure, extracted with ethyl acetate and there is obtained after the usual working-up the desired product as a diastereomer mixture (9:1), which is separated by chromatography. Yield: 30 mg (8%) of the less polar epimer of tert-butyl (4S,5R)-4-(cyclohexylmethyl)-5-[(1S or R,2S or R)-1,2-dihydroxycyclohexyl]-2,2-dimethyl-3-oxazolidinecarboxylate as an oil, $R_F$:0.3 (4:1 mixture of toluene and ethyl acetate as the eluent) and 330 mg (89%) of the more polar epimer tert-butyl (4S,5R)-4-(cyclohexylmethyl)-5-[(1R or S,2R or S)-1,2-dihydroxycyclohexyl]-2,2-dimethyl-3-oxazolidinecarboxylate as a foam, $R_F$:0.28 (4:1 mixture of toluene and ethyl acetate as the eluent).

310 mg (0.753 mmol) of tert-butyl (4S,5R)-4-(cyclohexylmethyl)-5-[(1S or R,2S or R)-1,2-dihydroxycyclohexyl]-2,2-dimethyl-3-oxazolidinecarboxylate (or tert-butyl (4S,5R)-4-(cyclohexylmethyl)-5-[(1R or S,2R or S)-1,2-dihydroxycyclohexyl]-2,2-dimethyl-3-oxazolidinecarboxylate) are dissolved in 8 ml of methanol, 4 ml of 2N hydrochloric acid are added thereto and the mixture is stirred at room temperature for 22 hours. The reaction mixture is then evaporated under reduced pressure, toluene is added thereto twice and evaporation under reduced pressure is carried out each time. In this manner there is obtained (1R or S,2R or S)-1-[(1R,2S)-1-amino-3-cyclohexyl-1-hydroxypropyl]-1;2-cyclohexanediol as an amorphous solid, $R_F$:0.15 (65:10:1 mixture of methylene chloride, methanol and ammonia as the eluent).

EXAMPLE A

A sterile filtered, aqueous solution of (R or S)-N-[(1S,2R,3S)-1-(cyclohexylmethyl)-3-cyclopropyl-2,3dihydroxypropyl]-8-propyl-α,6(3-pyridyl)-s-triazolo-[4,3-a]pyrazine-3-acetamide is mixed while warming with a sterile gelatin solution, which contains phenol as a preserving agent, under aseptic conditions so that 1.0 ml of solution has the following composition:

| | |
|---|---|
| (R or S)-4-[(1S,2R,3S)-1-(Cyclohexylmethyl))-3-cyclopropyl-2,3-dihydroxypropyl]-8-propyl-α,6-bis(3-pyridyl)-s-triazolo[4,3-a]pyrazine-3-acetamide | 3.0 mg |
| Gelatin | 150.0 mg |
| Phenol | 4.7 mg |
| Dist. Water ad | 1.0 ml |

The mixture is filled into 1.0 ml vials under aseptic conditions.

EXAMPLE B 5 mg of (R or S)-N-[(1S,2R,3S)-1-(cyclohexylmethyl)-3-cyclopropyl-2,3-dihydroxypropyl]-8-propyl-α,6-bis(3-pyridyl)-s-triazolo[4,3-a]pyrazine-3-acetamide are dissolved in 1 ml of an aqueous solution with 20 mg of mannitol. The solution is filtered sterile and filled under aseptic conditions into a 2 ml ampule, cooled to a low temperature and lyophilized. Prior to administration the lyophilizate is dissolved in 1 ml of distilled water or 1 ml of physiological saline. The solution is used intramuscularly or intravenously. This formulation can also be filled into double chamber injection ampules.

EXAMPLE C 500 mg of finely milled (R or S)-N-[(1S,2R,3S)-1-(cyclohexylmethyl)-3-cyclopropyl-2,3-dihydroxypropyl]-8-propyl-α,6-bis(3-pyridyl)-s-triazolo[4,3-a]pyrazine-3-acetamide are suspended in a mixture of 3.5 ml of Myglyol 812 and 0.08 g of benzyl alcohol. This suspension is filled into a container having a dosage valve. 5.0 g of Freon 12 are filled under pressure into the container through the valve. The Freon is dissolved in the Myglyolbenzyl alcohol mixture by shaking. This spray container contains about 100 single doses which can be applied individually.

EXAMPLE D

When the procedures described in Examples A–C are followed, corresponding galenical preparations can be prepared from the following, likewise preferred, compounds:

(R or S)-N-[(1S,2R,3S)-1-(Cyclohexylmethyl)-3-cyclopropyl-2,3-dihydroxypropyl]-8-isopropyl-α-(imidazol-4-ylmethyl)-6-(3-pyridyl)-s-triazolo[4,3-a]pyrazine-3-acetamide;

(R or S)-N-[(1S,2R,3S)-1-(cyclohexylmethyl)-3-cyclohexyl-2,3-dihydroxypropyl]-α-(imidazol-4-ylmethyl)-8-isobutyl-6-(3-pyridyl)-s-triazolo[4,3-a]pyrazine-3-acetate;

(R or S)-N-[(1S,2R,3S)-1-(cyclohexylmethyl)-2,3-dihydroxy-5-methylhexyl]-8-propyl-6-(3-pyridyl)-α-(3-pyridylmethyl)-s-triazolo[4,3-a]pyrazine-3-acetamide;

(S or R)-N-[(1S,2R,3S)-1-(cyclohexylmethyl)-3-cyclopropyl-2,3-dihydroxypropyl]-8-[(RS)-1-methylpropyl]-α-(3-pyridylmethyl)-6-(3-pyridyl)-s-triazolo[4,3-a]pyrazine-3-acetamide and N-[(1S,2R,3S)-1-(cyclohexylmethyl)-3-cyclopropyl-2,3-dihydroxypropyl]-8-[(RS)-1-methylpropyl]-6-(3-pyridyl)-s-triazolo[4,3-a]pyrazine-3-carboxamide.

We claim:
1. A compound of the formula wherein
one of A and B is nitrogen and the other is —CH— or both are nitrogen
X is nitrogen and Y is —CH—,
$R^1$ is phenyl, pyridyl or thienyl,
$R^2$ is alkyl or arylalkyl,
$R^3$ is hydrogen, alkyl, imidazol-2-ylmethyl, imidazol-4-ylmethyl, pyridylmethyl, pyrazol-3-ylmethyl, thien-2-ylmethyl, thiazol-4-ylmethyl, alkylthiomethyl, carbamoylmethyl, carbamoylethyl or benzyl,
$R^4$ is cyclohexylmethyl, benzyl or isobutyl, and
$R^5$ is selected from the group consisting of $$-(CH)_m-R^6 \quad \text{(a)}$$
$$\quad | \quad$$
$$OH$$

and (b) structure with OH, $(CH_2)_n$, OH, OH groups in which $R^6$ is cycloalkyl, alkyl, alkenyl or arylalkyl, m is the number 2 or 3 and n is the number 3 or 4, in the form of optically pure diastereomers, mixtures of diastereomers, diastereomeric racemates or mixtures of diastereomeric racemates as well as pharmaceutically acceptable salts of these compounds.

2. A compound according to claim 1, wherein A and B each are nitrogen.

3. A compound according to claim 1, wherein $R^1$ is pyridyl.

4. A compound according to claim 3, wherein $R^1$ is 3-pyridyl.

5. A compound according to claim 1, wherein $R^2$ is alkyl or phenylalkyl.

6. A compound according to claim 5, wherein $R^2$ is propyl, isopropyl, isobutyl, 1-methylpropyl or benzyl.

7. A compound according to claim 1, wherein $R^3$ is hydrogen, imidazol-2-ylmethyl, imidazol-4-ylmethyl or pyridylmethyl.

8. A compound according to claim 7, wherein $R^3$ is imidazol-4-ylmethyl or 3-pyridylmethyl.

9. A compound according to claim 1, wherein $R^4$ is cyclohexylmethyl.

10. A compound according to claim 1, wherein $R^5$ is group (a).

11. A compound according to claim 10, wherein m is number 2 and $R^6$ is cycloalkyl.

12. A compound according to claim 1, wherein A, B and X each are nitrogen, Y is —CH—, $R^1$ is 3-pyridyl, $R^2$ is propyl, isopropyl, isobutyl, 1-methylpropyl or benzyl, $R^3$ is imidazol-4-ylmethyl or pyridyl-3-methyl, $R^4$ is cyclohexylmethyl and $R^5$ is group (a) in which m is the number 2 and $R^6$ is cycloalkyl.

13. (R or S)-N-[(1S,2R,3S)-1-(Cyclohexylmethyl)-3-cyclopropyl-2,3-dihydroxypropyl]-8-propyl-α,6-bis(3-pyridyl)-s-triazolo[4,3-a]pyrazine-3-acetamide.

14. (R or S)-N-[(1S,2R,3S)-1-(Cyclohexylmethyl)-3-cyclopropyl-2,3-dihydroxypropyl]-8-isopropyl-α-(imidazol-4-ylmethyl)-6-(3-pyridyl)-s-triazolo[4,3-a]pyrazine-3-acetamide.

15. (R or S)-N-[(1S,2R,3S)-1-(Cyclohexylmethyl)-3-cyclohexyl-2,3-dihydroxypropyl]-α-(imidazol-4-ylmethyl)-8-isobutyl-6-(3-pyridyl)-s-triazolo[4,3-a]pyrazine-3-acetate.

16. (R or S)-N-[(1S,2R,3S)-1-(Cyclohexylmethyl)-2,3-dihydroxy-5-methylhexyl]-8-propyl-6-(3-pyridyl)-α-(3-pyridylmethyl)-s-triazolo[4,3-a]pyrazine-3-acetamide.

17. (S or R)-N-[(1S,2R,3S)-1-(Cyclohexylmethyl)-3-cyclopropyl-2,3-dihydroxypropyl]-8-[(RS)-1-methylpropyl]-α-(3-pyridylmethyl)-6-(3-pyridyl)-s-triazolo[4,3-a]pyrazine-3-acetamide.

18. N-[(1S,2R,3S)-1-(Cyclohexylmethyl)-3-cyclopropyl-2,3-dihydroxypropyl]-8-[(RS)-1-methylpropyl]-6-(3-pyridyl)-s-triazolo[4,3-a]pyrazine-3-carboxamide.

19. A compound of the formula

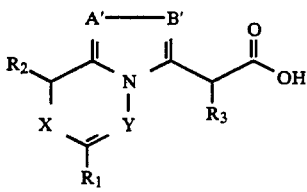

III wherein one of A' and B' is nitrogen and the other is —CH—; and, X is nitrogen and Y is —CH—, $R^1$ is phenyl, pyridyl or thienyl; $R^2$ is alkyl or arylalkyl; $R^3$ is hydrogen, alkyl, imidazol-2-ylmethyl, imidazol-4-ylmethyl, pyridylmethyl, pyrazol-3-ylmethyl, thien-2-ylmethyl, thiazol-4-ylmethyl, alkylthiomethyl, carbamoylmethyl, carbamoylethyl or benzyl.

20. A pharmaceutical composition comprising an effective amount of a compound of the formula

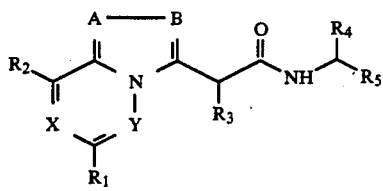

I wherein
one of A and B is nitrogen and the other is —CH— or both are nitrogen
X is nitrogen and Y is —CH—,
$R^1$ is phenyl, pyridyl or thienyl,
$R^2$ is alkyl or arylalkyl,
$R^3$ is hydrogen, alkyl, imidazol-2-ylmethyl, imidazol-4-ylmethyl, pyridylmethyl, pyrazol-3-ylmethyl, thien-2-ylmethyl, thiazol-4-ylmethyl, alkylthiomethyl, carbamoylmethyl, carbamoylethyl or benzyl,
$R^4$ is cyclohexylmethyl, benzyl or isobutyl, and
$R^5$ is selected from the group consisting of

(a)

and

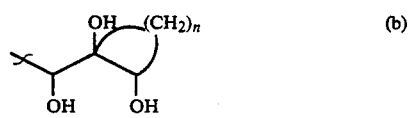

(b)

in which $R^6$ is cycloalkyl, alkyl, alkenyl or arylalkyl,
m is the number 2 or 3 and n is the number 3 or 4, in the form of optically pure diastereomers, mixtures of diastereomers, diastereomeric racemates or mixtures of diastereomeric racemates as well as pharmaceutically acceptable salts of these compounds and an inert carrier.

21. A pharmaceutical composition according to claim 20, wherein A and B each are notrogen.

22. A pharmaceutical composition according to claim 20, wherein $R^1$ is pyridyl.

23. A pharmaceutical composition according to claim 22, wherein $R^1$ is 3-pyridyl.

24. A pharmaceutical composition according to claim 20, wherein $R^2$ is alkyl or phenylalkyl.

25. A pharmaceutical composition according to claim 24, wherein $R^2$ is propyl, isopropyl, isobutyl, 1-methylpropyl or benzyl.

26. A pharmaceutical composition according to claim 20, wherein $R^3$ is hydrogen, imidazol-2-ylmethyl, imidazol-4-ylmethyl or pyridylmethyl.

27. A pharmaceutical composition according to claim 26, wherein $R^3$ is imidazol-4-ylmethyl or 3-pyridylmethyl.

28. A pharmaceutical composition according to claim 20, wherein $R^4$ is cyclohexylmethyl.

29. A pharmaceutical composition according to claim 20, wherein $R^5$ is group (a).

30. A pharmaceutical composition according to claim 29, wherein m is the number 2 and $R^6$ is cycloalkyl.

31. A pharmaceutical composition according to claim 20, wherein A, B and X each are nitrogen, Y is —CH—, $R^1$ is 3-pyridyl, $R^2$ is propyl, isopropyl, isobutyl, 1-methylpropyl or benzyl, $R^3$ is imidazol-4-ylmethyl or 3-pyridylmethyl, $R^4$ is cyclohexylmethyl and $R^5$ is group (a) in which m is the number 2 and $R^6$ is cycloalkyl.

32. A method of inhibiting renin comprising administering an effective amount of a compound of the formula

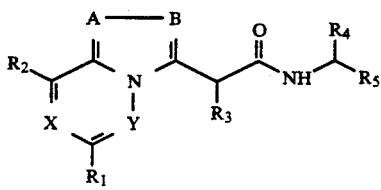

wherein
one of A and B is nitrogen and the other is —CH— or both
are nitrogen
X is nitrogen and Y is —CH—,
$R^1$ is phenyl, pyridyl, or thienyl,
$R^2$ is alkyl or arylalkyl,
$R^3$ is hydrogen, alkyl, imidazol-2-ylmethyl, imidazol-4-ylmethyl, pyridylmethyl, pyrazol-3-ylmethyl, thien-2-ylmethyl, thiazol-4-ylmethyl, alkylthiomethyl, carbamoylmethyl, carbamoylethyl or benzyl,
$R^4$ is cyclohexylmethyl, benzyl or isobutyl, and
$R^5$ is selected from the group consisting of

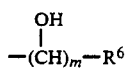 (a)

and

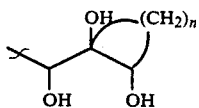 (b)

in which $R^6$ is cycloalkyl, alkyl, alkenyl or arylalkyl,
m is the number 2 or 3 and n is the number 3 or 4, in the form of optically pure diastereomers, mixtures of diastereomers, diastereomeric racemates or mixtures of diastereomeric racemates as well as pharmaceutically acceptable salts of these compounds.

33. A method according to claim 32, wherein A and B each are nitrogen.

34. A method according to claim 32, wherein $R^1$ is pyridyl.

35. A method according to claim 34, wherein $R^1$ is 3-pyridyl.

36. A method according to claim 32, wherein $R^2$ is alkyl or phenylalkyl.

37. A method according to claim 36, wherein $R^2$ is propyl, isopropyl, isobutyl, 1-methylpropyl or benzyl.

38. A method according to claim 32, wherein $R^3$ is hydrogen, imidazol-2-ylmethyl, imidazol-4-ylmethyl or pyridylmethyl.

39. A method according to claim 38, wherein $R^3$ is imidazol-4-ylmethyl or pyridyl-3-methyl.

40. A method according to claim 32, wherein $R^4$ is cyclohexylmethyl.

41. A method according to claim 32, wherein $R^5$ is group (a).

42. A method according to claim 41, wherein m is the number 2 and $R^6$ is cycloalkyl.

43. A method according to claim 32, wherein A, B and X each is nitrogen, Y is —CH—, $R^1$ is 3-pyridyl, $R^2$ is propyl, isopropyl, isobutyl, 1-methylpropyl or benzyl, $R^3$ is imidazol-4-ylmethyl or pyridyl-3-methyl, $R^4$ is cyclohexylmethyl and $R^5$ is group (a) in which m is the number 2 and $R^6$ is cycloalkyl.

44. A method of treating or preventing high blood pressure or cardiac insufficiency which comprises administering to a host in need of such treatment an effective amount of the formula

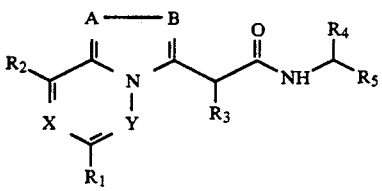 I wherein
one of A and B is nitrogen and the other is —CH— or both are nitrogen
X is nitrogen and Y is —CH—,
$R^1$ is phenyl, pyridyl, or thienyl,
$R^2$ is alkyl or arylalkyl,
$R^3$ is hydrogen, alkyl, imidazol-2-ylmethyl, imidazol-4-ylmethyl, pyridylmethyl, pyrazol-3-ylmethyl, thien-2-ylmethyl, thiazol-4-ylmethyl, alkylthiomethyl, carbamoylmethyl, carbamoylethyl or benzyl,
$R^4$ is cyclohexylmethyl, benzyl or isobutyl, and
$R^5$ is selected from the group consisting of

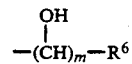 (a)

and

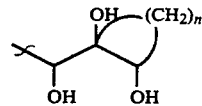 (b)

in which $R^6$ is cycloalkyl, alkyl, alkenyl or arylalkyl,
m is the number 2 or 3 and n is the number 3 or 4, in the form of optically pure diastereomers, mixtures of diastereomers, diastereomeric racemates or mixtures of diastereomeric racemates as well as pharmaceutically acceptable salts of these compounds.

45. A method according to claim 44, wherein A and B each are nitrogen.

46. A method according to claim 44, wherein $R^1$ is pyridyl.

47. A method according to claim 46, wherein $R^1$ is 3-pyridyl.

48. A method according to claim 44, wherein $R^2$ is alkyl or phenylalkyl.

49. A method according to claim 48, wherein $R^2$ is propyl, isopropyl, isobutyl, 1-methylpropyl or benzyl.

50. A method according to claim 44, wherein $R^3$ is hydrogen, imidazol-2-ylmethyl, imidazol-4-ylmethyl or pyridylmethyl.

51. A method according to claim 50, wherein $R^3$ is imidazol-4-ylmethyl or 3-pyridylmethyl.

52. A method according to claim 44, wherein $R^4$ is cyclohexylmethyl.

53. A method according to claim 44, wherein $R^5$ is group (a).

54. A method according to claim 53, wherein m is the number 2 and $R^6$ is cycloalkyl.

55. A method according to claim 44, wherein A, B and X each is nitrogen, Y is —CH—, $R^1$ is 3-pyridyl, $R^2$ is propyl, isopropyl, isobutyl, 1-methylpropyl or benzyl, $R^3$ is imidazol-4-ylmethyl or pyridyl-3-methyl, $R^4$ is cyclohexylmethyl and $R^5$ is group (a) in which m is the number 2 and $R^6$ is cycloalkyl.

* * * * *